(12) United States Patent
Xian et al.

(10) Patent No.: US 9,950,032 B2
(45) Date of Patent: Apr. 24, 2018

(54) COMPOSITIONS AND METHODS FOR LUNG REGENERATION

(71) Applicants: **AGENCY FOR SCIENCE, TECHNOLOGY AND RESEARCH (A*STAR), Connexis (SG); MULTICLONAL THERAPEUTICS**, Newburyport, MA (US)

(72) Inventors: Wa Xian, Farmington, CT (US); Frank McKeon, Farmington, CT (US); Matthew Vincent, Newburyport, MA (US)

(*) Notice: Subject to any disclaimer, the term of this patent is extended or adjusted under 35 U.S.C. 154(b) by 0 days.

(21) Appl. No.: 14/354,594

(22) PCT Filed: Oct. 29, 2012

(86) PCT No.: PCT/US2012/062387
§ 371 (c)(1),
(2) Date: Apr. 27, 2014

(87) PCT Pub. No.: WO2013/066802
PCT Pub. Date: May 10, 2013

(65) Prior Publication Data
US 2015/0125490 A1 May 7, 2015

Related U.S. Application Data

(60) Provisional application No. 61/552,220, filed on Oct. 27, 2011, provisional application No. 61/552,639, filed on Oct. 28, 2011, provisional application No. 61/604,807, filed on Feb. 29, 2012.

(51) Int. Cl.

| | | |
|---|---|---|
| C12Q 1/02 | (2006.01) |
| C12N 5/02 | (2006.01) |
| G01N 33/567 | (2006.01) |
| C12N 5/00 | (2006.01) |
| C40B 30/04 | (2006.01) |
| A61K 38/17 | (2006.01) |
| A61K 35/28 | (2015.01) |
| C12N 5/071 | (2010.01) |
| A61K 31/381 | (2006.01) |
| A61K 31/4164 | (2006.01) |
| A61K 45/06 | (2006.01) |
| G01N 33/50 | (2006.01) |
| A61K 31/00 | (2006.01) |
| A61K 38/00 | (2006.01) |

(52) U.S. Cl.
CPC ........ *A61K 38/1709* (2013.01); *A61K 31/381* (2013.01); *A61K 31/4164* (2013.01); *A61K 35/28* (2013.01); *A61K 45/06* (2013.01); *C12N 5/0689* (2013.01); *G01N 33/5073* (2013.01); *A61K 31/00* (2013.01); *A61K 38/00* (2013.01); *C12N 2506/00* (2013.01); *C40B 30/04* (2013.01); *G01N 2500/10* (2013.01)

(58) Field of Classification Search
CPC ...... A61K 31/00; A61K 38/00; C12N 5/0689; C12N 2506/00; C40B 30/04; G01N 33/5073; G01N 2500/10
USPC ....................... 435/7.21, 29, 325, 377; 506/9
See application file for complete search history.

(56) References Cited

U.S. PATENT DOCUMENTS

2004/0109844 A1* 6/2004 Costa et al.
2010/0010056 A1* 1/2010 Rehan et al.

OTHER PUBLICATIONS

Rock et al., 2009, PNAS, vol. 106, No. 31, p. 12771-12775.*
Hackett et al., May 2011, PLoS ONE, vol. 6, No. 5, e18378, p. 1-22.*

* cited by examiner

*Primary Examiner* — Shin Lin Chen
(74) *Attorney, Agent, or Firm* — Nelson Mullins Riley & Scarborough LLP; Anthony A. Laurentano

(57) ABSTRACT

Airway stem cells have been implicated in the pathology and progression of chronic airway diseases and yet also hold the promise of physiological and ultimately therapeutic repair of damage wrought by these conditions. The present invention is based on the observation that certain p63-expressing stem cells in the bronchiolar epithelium undergo rapid proliferation after infection and radiate to interbronchiolar regions of alveolar ablation. Once there, these cells assemble into discrete, Krt5+ pods and initiate expression of markers typical of alveoli. The dynamics of this p63-expressing stem cell in lung regeneration mirrors parallel findings that defined pedigrees of human distal airway stem cells assemble alveoli-like structures in vitro and provides new therapeutic avenues to acute and chronic airway disease as well as identifying agents which can promote repair.

6 Claims, 12 Drawing Sheets

Figure 11A

TASC Signature

| Gene Symbol | p-value | Fold-Change(TASC vs. DASC) |
|---|---|---|
| *TMPRSS11D | 7.03E-07 | 29.7703 |
| SPRR1A | 1.44E-06 | 24.4047 |
| SPRR2C | 6.17E-07 | 20.5046 |
| *KRT6A | 5.78E-07 | 16.3986 |
| *TMPRSS11B | 3.87E-07 | 14.9493 |
| CRNN | 2.80E-05 | 13.0657 |
| MT1L | 0.000489486 | 12.6329 |
| USP6 | 0.000121694 | 11.7649 |
| RGS2 | 2.55E-06 | 10.9295 |
| SPINK7 | 8.58E-05 | 10.7646 |
| STARD4 | 1.42E-06 | 9.95315 |
| RAET1L | 0.000287793 | 9.88988 |
| *TMPRSS11A | 1.37E-05 | 9.73362 |
| *DSG3 | 1.59E-08 | 9.00731 |
| ZBED2 | 9.47E-05 | 7.9196 |
| *ERAP2 | 7.17E-07 | 7.69252 |
| HMGCS1 | 9.72E-06 | 7.63513 |
| HLA-C | 1.79E-05 | 7.6308 |
| *POF1B | 6.88E-07 | 7.57532 |
| *GLIPR1 | 1.74E-06 | 7.47008 |
| POPDC3 | 0.000584655 | 6.98849 |
| *PRAC | 0.000111292 | 6.84123 |
| CCDC144A | 0.000825603 | 6.78438 |
| KLK6 | 3.49E-05 | 6.52463 |
| LASS3 | 1.60E-06 | 6.21085 |
| BCAT1 | 1.67E-06 | 6.07267 |
| MMP10 | 1.03E-05 | 5.81306 |
| GJB6 | 3.32E-07 | 5.77245 |
| A2ML1 | 0.000667931 | 5.69143 |
| DNAJC15 | 4.15E-06 | 5.50529 |
| *IFI44 | 4.60E-07 | 5.17531 |
| SLFN13 | 4.06E-06 | 5.08375 |
| TMTC1 | 2.44E-05 | 4.9664 |
| COL12A1 | 8.00E-08 | 4.93866 |
| PTHLH | 1.28E-05 | 4.9038 |
| ECM1 | 8.40E-05 | 4.83907 |
| SLFN11 | 1.26E-06 | 4.79127 |
| KRT14 | 3.19E-07 | 4.79094 |
| SCG5 | 1.73E-05 | 4.70702 |
| TMPRSS11E | 0.000821669 | 4.67233 |
| *TBN2 | 2.72E-05 | 4.15269 |
| *ECM1 | 8.40E-05 | 4.83907 |
| *KRT13 | 0.00745423 | 4.07872 |

Figure 11B

DASC Signature

| Gene Symbol | p-value | Fold-Change(DASC vs TASC) |
|---|---|---|
| GSTA2 | 6.70E-06 | 130.893 |
| GSTA1 | 9.81E-07 | 42.6899 |
| *LMO3 | 1.75E-08 | 40.8243 |
| PPARGC1A | 2.78E-08 | 21.4615 |
| RPS15A | 0.0244778 | 18.9258 |
| ALDH1A1 | 5.59E-08 | 18.7274 |
| *SCGB1A1 | 5.28E-05 | 18.1001 |
| TF | 2.63E-06 | 10.1834 |
| GOLGA8A | 8.42E-06 | 9.14632 |
| ATP5L | 0.0190024 | 8.39835 |
| LSM3 | 0.00283319 | 7.84288 |
| CP | 0.000148531 | 7.56011 |
| SLC34A2 | 0.000137024 | 7.47741 |
| KRT15 | 9.61E-06 | 6.88251 |
| RPL18 | 0.00405378 | 6.84999 |
| RPL14 | 0.01627 | 6.69458 |
| *SAA1 | 1.70E-06 | 6.0607 |
| TMEM14C | 0.00600444 | 5.80962 |
| HINT1 | 0.00592648 | 5.64451 |
| BNIP3 | 0.0122902 | 5.62118 |
| COMMD6 | 0.0367675 | 5.51012 |
| *SERPINF1 | 4.07E-07 | 5.20435 |
| CYP4B1 | 8.70E-07 | 5.06866 |
| LYPLA1 | 0.000328677 | 5.01599 |
| TXNIP | 1.81E-05 | 5.00165 |
| RAP1B | 0.0280893 | 4.98122 |
| TRIM22 | 2.79E-06 | 4.88373 |
| CHCHD3 | 0.0144078 | 4.7623 |
| RPL17 | 0.0204879 | 4.69287 |
| S100P | 0.00456373 | 4.64782 |
| CCDC146 | 4.50E-05 | 4.63141 |
| SERPINB3 | 1.44E-05 | 4.53137 |
| SH3PXD2A | 0.0314038 | 4.35029 |
| OAPIN1 | 0.00286368 | 4.33304 |
| CYP1B1 | 0.000900564 | 4.27465 |
| SF3B5 | 0.000387497 | 4.19474 |
| FAM46C | 0.00065419 | 4.18709 |
| STEAP4 | 0.00381719 | 4.15361 |
| WFDC2 | 0.000125701 | 4.1281 |
| *C4orf18 | 0.000166752 | 3.783 |
| *SPRY1 | 0.000583069 | 3.60757 |
| *OR4B3 | 8.46E-05 | 3.27823 |
| *ADAM28 | 0.000389122 | 2.96755 |
| *KLK7 | 0.00547097 | 2.90156 |

Figure 15A

Pathways enriched in Cluster A (515 genes ) by GO with p< 0.02

Cluster A

| Pathways | % of cluster A | % of whole genome | p value |
|---|---|---|---|
| Fructose galactose metabolism | 0.66 | 0.05 | 0.00203 |
| Glutamine glutamate conversion | 0.44 | 0.02 | 0.0036 |
| PI3 kinase pathway | 1.31 | 0.42 | 0.0138 |
| Axon guidance mediated by netrin | 0.66 | 0.11 | 0.0149 |
| Insulin/IGF pathway-protein kinase B signaling cascade | 1.09 | 0.32 | 0.0162 |
| Flavin biosynthesis | 0.22 | 0.00 | 0.0173 |

Pathways enriched in Cluster B (281 genes ) by GO with p< 0.02

Cluster B

| Pathways | % of cluster B | % of whole genome | p value |
|---|---|---|---|
| 5-Hydroxytryptamine degradation | 1.01 | 0.08 | 0.00003429 |
| Phenylethylamine degradation | 1.53 | 0.05 | 0.000014 |
| Alzheimer disease-presenilin pathway | 3.05 | 0.47 | 0.000431 |
| Endothelin signaling pathway | 2.29 | 0.34 | 0.000312 |
| Angiogenesis | 3.05 | 0.74 | 0.000827 |
| Cadherin signaling pathway | 2.67 | 0.64 | 0.00163 |
| Hedgehog signaling pathway | 1.15 | 0.10 | 0.00214 |
| Wnt signaling pathway | 3.44 | 1.33 | 0.00808 |
| GABA-B receptor II signaling | 1.15 | 0.16 | 0.00957 |
| EGF receptor signaling pathway | 1.91 | 0.53 | 0.0132 |
| Beta2 adrenergic receptor signaling pathway | 1.15 | 0.19 | 0.0136 |
| Beta1 adrenergic receptor signaling pathway | 1.15 | 0.19 | 0.0136 |
| Heterotrimeric G-protein signaling pathway-Gi alpha and Gs alpha mediated pathway | 1.91 | 0.53 | 0.0136 |
| TCA cycle | 0.76 | 0.07 | 0.0144 |
| Nicotinic acetylcholine receptor signaling pathway | 1.53 | 0.37 | 0.0176 |
| Metabotropic glutamate receptor group II pathway | 1.15 | 0.21 | 0.0184 |
| Succinate to propionate conversion | 0.38 | 0.01 | 0.0198 |

Figure 15B

Pathways enriched in Cluster C (600 genes) by GO with p< 0.02

Cluster C

| Pathways | % of cluster C | % of whole genome | P value |
|---|---|---|---|
| Integrin signaling pathway | 4.08 | 0.71 | 4.06E-11 |
| Angiogenesis | 3.72 | 0.74 | 2.92E-09 |
| Nicotinic acetylcholine receptor signaling pathway | 2.13 | 0.37 | 0.00000217 |
| Alzheimer disease-presenilin pathway | 2.13 | 0.47 | 0.0000222 |
| Axon guidance mediated by semaphorins | 1.24 | 0.17 | 0.0000582 |
| VEGF signaling pathway | 1.24 | 0.29 | 0.00149 |
| Inflammation mediated by chemokine and cytokine signaling pathway | 2.66 | 1.14 | 0.00247 |
| PDGF signaling pathway | 1.60 | 0.62 | 0.00646 |
| Axon guidance mediated by Slit/Robo | 0.53 | 0.08 | 0.011 |
| B cell activation | 1.06 | 0.33 | 0.0123 |

Pathways enriched in Cluster D (809 genes) by GO with p< 0.02

Cluster D

| Pathways | % of cluster D | % of whole genome | P value |
|---|---|---|---|
| Inflammation mediated by chemokine and cytokine signaling pathway | 4.40 | 1.14 | 2.11E-10 |
| T cell activation | 3.02 | 0.54 | 2.2E-10 |
| B cell activation | 2.34 | 0.30 | 8.35E-10 |
| Toll receptor signaling pathway | 1.37 | 0.24 | 0.0000160 |
| DNA replication | 0.69 | 0.10 | 0.000754 |
| PDGF signaling pathway | 1.79 | 0.62 | 0.000775 |
| Integrin signaling pathway | 1.79 | 0.71 | 0.00246 |
| JAK/STAT signaling pathway | 0.55 | 0.08 | 0.00255 |
| p53 pathway feedback loops 2 | 0.82 | 0.19 | 0.00336 |
| EGF receptor signaling pathway | 1.37 | 0.53 | 0.00604 |
| Heterotrimeric G-protein signaling pathway-Gq alpha and Go alpha mediated pathway | 1.37 | 0.50 | 0.00633 |
| Apoptosis signaling pathway | 0.55 | 0.54 | 0.00696 |
| Axon guidance mediated by netrin | 1.24 | 0.11 | 0.00927 |
| FGF signaling pathway | 1.24 | 0.48 | 0.00929 |
| Interferon-gamma signaling pathway | 0.55 | 0.11 | 0.0104 |
| Thyrotropin-releasing hormone receptor signaling pathway | 0.82 | 0.27 | 0.0155 |

SEQUENCE LISTING

```
<160> NUMBER OF SEQ ID NOS: 1

<210> SEQ ID NO 1
<211> LENGTH: 256
<212> TYPE: PRT
<213> ORGANISM: Homo sapiens

<400> SEQUENCE: 1

Met Phe Gln Thr Gly Gly Leu Ile Val Phe Tyr Gly Leu Leu Ala Gln
1               5                   10                  15

Thr Met Ala Gln Phe Gly Gly Leu Pro Val Pro Leu Asp Gln Thr Leu
            20                  25                  30

Pro Leu Asn Val Asn Pro Ala Leu Pro Leu Ser Pro Thr Gly Leu Ala
        35                  40                  45
```

-continued

```
Gly Ser Leu Thr Asn Ala Leu Ser Asn Gly Leu Leu Ser Gly Gly Leu
     50                  55                  60
Leu Gly Ile Leu Glu Asn Leu Pro Leu Leu Asp Ile Leu Lys Pro Gly
 65              70                  75                  80
Gly Gly Thr Ser Gly Gly Leu Leu Gly Gly Leu Leu Gly Lys Val Thr
             85                  90                  95
Ser Val Ile Pro Gly Leu Asn Asn Ile Ile Asp Ile Lys Val Thr Asp
            100                 105                 110
Pro Gln Leu Leu Glu Leu Gly Leu Val Gln Ser Pro Asp Gly His Arg
            115                 120                 125
Leu Tyr Val Thr Ile Pro Leu Gly Ile Lys Leu Gln Val Asn Thr Pro
            130                 135                 140
Leu Val Gly Ala Ser Leu Leu Arg Leu Ala Val Lys Leu Asp Ile Thr
145                 150                 155                 160
Ala Glu Ile Leu Ala Val Arg Asp Lys Gln Glu Arg Ile His Leu Val
                165                 170                 175
Leu Gly Asp Cys Thr His Ser Pro Gly Ser Leu Gln Ile Ser Leu Leu
            180                 185                 190
Asp Gly Leu Gly Pro Leu Pro Ile Gln Gly Leu Leu Asp Ser Leu Thr
            195                 200                 205
Gly Ile Leu Asn Lys Val Leu Pro Glu Leu Val Lys Gly Asn Val Cys
            210                 215                 220
Pro Leu Val Asn Glu Val Leu Arg Gly Leu Asp Ile Thr Leu Val His
225                 230                 235                 240
Asp Ile Val Asn Met Leu Ile His Gly Leu Gln Phe Val Ile Lys Val
                245                 250                 255
```

COMPOSITIONS AND METHODS FOR LUNG REGENERATION

FIELD

The invention provides compositions and methods for treating pulmonary conditions and for reducing and/or reversing the negative effects of pulmonary inflammation, exposure to damaging agents or as may be caused by an infectious agent.

BACKGROUND

The pulmonary system provides homeostasis and repair of the lung in response to attack by pathogens, toxins, pollutants, and other types of injuries.

Asthma is a non-infectious chronic inflammatory disease of the respiratory system characterized by a reversible airways obstruction. Acute airway obstruction, bronchial hyper-responsiveness and inflammatory state of the bronchial mucosa with increased levels of inflammatory mediators, are the most evident phenomenon which characterizes this pathology. Despite the increase in the prescribed anti-asthmatic treatments, the current trends indicate asthma is set to be the most chronic disease in industrialized countries, affecting mostly the children (10%) than the adults (15%).

Chronic obstructive pulmonary disease (COPD) is the most common of all the respiratory disorders in the world, which embraces several inflammatory pathologies that often co-exist. The WHO predicts COPD will become the third most common cause of death world over by 2020 accounting 8.4 million lives. Although asthma for the last 25 years has been managed therapeutically, with a combined bronchodilator and anti-inflammatory therapies, in contrast to this COPD have no effective treatments currently, while the efficacy of the corticosteroids is controversial. Hence, there is an urgent need to develop novel anti-inflammatory drugs having both the bronchodilatory and anti-inflammatory activity, having applicability to treat both COPD as well as asthma. Thus, the development of therapies for bronchial asthma has become the major focus of the pharmaceutical industry in the field of respiratory disorders.

Airway stem cells have been implicated in the pathology and progression of chronic airway diseases and yet also hold the promise of physiological and ultimately therapeutic repair of damage wrought by these conditions. Chronic airway disease is often regiospecific with allergic rhinitis affecting the sinuses, asthma, cystic fibrosis, and bronchiolitis obliterans in the large conducting tubes such as the bronchi and bronchioles, and COPD, pulmonary fibrosis, and pulmonary hypertension affecting the distal regions of the airways involved in oxygen exchange. A major focus of airway pathology therefore is to understand if and how stem cells initiate repair programs, participate in airway epithelial remodeling seen in chronic conditions, and mechanisms underlying defects in repair as in pulmonary fibrosis.

SUMMARY

The present disclosure is based on the observation that certain p63-expressing stem cells in the bronchiolar epithelium undergo rapid proliferation after infection and radiate to interbronchiolar regions of alveolar ablation. Once there, these cells assemble into discrete, Krt5+ pods and initiate expression of markers typical of alveoli. Gene expression profiles of these pods suggest that they are intermediates in the reconstitution of the alveolar-capillary network, such as which may be eradicated by viral infection. The dynamics of this p63-expressing stem cell in lung regeneration mirrors parallel findings that defined pedigrees of human distal airway stem cells assemble alveoli-like structures in vitro and suggests new therapeutic avenues to acute and chronic airway disease.

To address questions germane to adult stem cells in general, the inventors isolated and cloned various human airway stem cells from single cells and performed a pedigree-defined analysis of their lineage commitment, developmental potential, and gene expression profiles. These studies reveal three regiospecific stem cell types united by a common, p63-expressing basal phenotype and yet distinguished by expression profiles. Stem cell pedigrees from the distal airways show a remarkable ability in vitro to form either alveoli-like structures or bronchiolar epithelium, while those of proximal airways beget upper airway cell types or squamous metaplasia. Pedigree tracking of single cell-derived clones permits the decoding of adult stem cell repertoires to answer basic questions of lineage commitment, developmental plasticity, and their specific roles in repair and disease.

One aspect of the invention provides a composition comprising a clonal population of airway epithelial stem cells, which cells are keratin 5 (Krt5) positive and p63 positive, can propagate for at least 10 doublings, and more preferably at least 20, 30, 40, 50 or even 60 doublings, while maintaining a pluripotent phenotype, and can differentiate into airway epithelia.

Another aspect of the invention provides a composition of purified airway epithelial stem cells, which cells are keratin 5 (Krt5) positive and p63 positive, can propagate for at least 10 doublings, and more preferably at least 20, 30, 40, 50 or even 60 doublings, while maintaining a pluripotent phenotype, and can differentiate into airway epithelia.

Still another aspect of the invention provides a composition comprising at least $10^4$ (and more preferably $10^5$, $10^6$, $10^7$, $10^8$ or even $10^9$) airway epithelial stem cells, which cells are keratin 5 (Krt5) positive and p63 positive, can propagate for at least 10 doublings, and more preferably at least 20, 30, 40, 50 or even 60 doublings, while maintaining a pluripotent phenotype, and can differentiate into airway epithelia.

In certain embodiments, the airway epithelial stem cells are nasal epithelial stem cells (NESCs).

In other embodiments, the airway epithelial stem cells are trachael airway stem cells (TASCs).

In still other embodiments, the airway epithelial stem cells are distal airway stem cell (DASC).

In certain preferred embodiments, the NESC, TASC or DASC cell population can be characterized by the detectable expression of markers, or by the relative levels of one or more mRNA (relative to other stem cells or to normal lung tissue, such as aveoli). Exemplary expression profiles that can be used to distinguish stem cell populations are provided in the examples and figures. To further illustrate, in certain preferred embodiments of DASCs, the stem cells are also characterized as having mRNA levels for one or more, and preferably each of, PLUNC, SCGB3A1, GPX2, LTF, SCGB3A2, CYP2F2 and/or GABRP at least two times greater (more preferably three, five, ten or even twenty times greater) than levels in normal differentiated alveoli cells.

In preferred embodiments, the airway epithelial stem cells are mammalian cells, and even more preferably human cells.

In certain embodiments, the airway epithelial stem cells are isolated from adult tissue. However, it is specifically contemplated that the stem cells can be derived from any source of pluripotent stem cell, such as embryonic stem cells, induced pluripotency stem (iPS) cells and fetal stem cells, as well as by dedifferentiation of adult tissues, particularly adult lung tissues.

The present invention also provides for the use of the subject airway epithelial stem cells for use in pharmaceutical formulations. For instance, it is specifically contemplated that the cells of the present invention can be used in the manufacture of a medicament for promoting lung tissue regeneration and/or slowing the rate of lung tissue degeneration. Such compositions will be suitable for use in human patients, i.e., highly pure with respect to the stem cell population and being pyrogen-free.

The disclosure further provides a composition comprising a clonal population of NESC stem cells (which can be isolated from nasal turbinate), wherein the stem cells differentiate into goblet and ciliated cells. Preferably the composition, with respect to the cellular component, is at least 50 percent stem cell, more preferably at least 75, 80, 85, 90, 95 or even 99 percent stem cell. The stem cells can be pluripotent, multipotent or oligopotent.

The disclosure further provides a composition comprising a clonal population of TASC stem cells (which can be isolated from tracheobronchial epithelia) that can differentiate into goblet and ciliated cells. In certain preferred embodiments, the stem cells are characterized as having an mRNA profile that is positive for expression one or more of TMRSS11D, SPRR1A, SPRR2C, KRTDAP, TMPRSS11B, CRNN and MT1L mRNA, i.e., mRNA present at detectable levels, and more preferably at levels (i.e., relative to actin expression) that are greater than in the tracheobronchial stem cells than in stem cells isolated from distal airway tissue. Preferably the composition, with respect to the cellular component, is at least 50 percent stem cell, more preferably at least 75, 80, 85, 90, 95 or even 99 percent stem cell. The stem cells can be pluripotent, multipotent or oligopotent.

The disclosure further provides a composition comprising a clonal population of DASC stem cells (which can be isolated from distal airway tissue), wherein the stem cells differentiate into alveolar type lung cells and/or Clara cells. Preferably the composition, with respect to the cellular component, is at least 50 percent stem cell, more preferably at least 75, 80, 85, 90, 95 or even 99 percent stem cell. The stem cells can be pluripotent, multipotent or oligopotent. In certain preferred embodiments, the stem cells are characterized as having an mRNA profile including expression of GSTA2, GSTA1, LMO3, PPARGC1A, RPS15A, ALDH1A1 and SCGB1A1 mRNA at detectable levels, and more preferably at levels (i.e., relative to actin expression) that are greater than stem cells isolated from tracheobronchial epithelia. Preferably all five genes have an mRNA profile in that range. In certain embodiments, the mRNA transcript profile for the stem cells will also be characterized by detectable levels of KRT5.

The disclosure further provides a method of screening for an agent effective in causing lung regeneration including the steps of providing a population of distal airway stem cells (DASCs), wherein the DASCs are able to differentiate into alveolar type lung cells and/or Clara cells; providing a test agent; and exposing the stem cells to the test agent; wherein if the test agent to increases viability, growth, migration or differentiation of the DASCs, the test agent is an agent effective in regeneration of lung.

In certain embodiments, the test agent is also contacted with normal cells or tissue of the lung, and the differential ability, if any, of the test agent to increase the viability, growth, migration or differentiation of the normal cells or tissue is compared to that with the DASCs.

In certain embodiments, the DASCs are mammalian DASCs, such as human DASCs or rat DASCs.

The DASCs can be clonal, and can be pluripotent, multipotent or oligopotent. In certain preferred embodiments, the stem cells are characterized as having an mRNA profile that includes upregulated expression of PLUNC, SCGB3A1, GPX2, LTF, SCGB3A2, CYP2F2 and/or GABRP mRNA in mRNA, which are expressed at least ten or twenty times greater than in normal alveoli. Preferably all seven genes have an mRNA profile in that range. In certain embodiments, the mRNA transcript profile for the stem cells will also be characterized by detectable levels of KRT5.

Another aspect of the invention is based on the observations that DASCs can cause repair and/or remodeling of damaged lung tissue in a distal manner, indicating the role of one or more paracrine factors. When compared to NESCs and TASCs, DASCs had a profoundly increased potency for inducing tissue regeneration, further indicating that the secretion of relevant paracrine factor(s) were upregulated in the DASCs as compared to the other two stem cell populations. Accordingly, it is contemplated that the use of one or more therapeutic agents which are derived from the secreted proteins of the DASC population can be used to treat or prevent diseases and disorders involving airway tissue. A list of genes which are upregulated in DASCs is provided in Table 1 below. Airway therapeutics contemplated by the present invention include polypeptides encoded by the upregulated genes, fragments and analogs of those polypeptides, and agonists or mimetics of those proteins.

The stem cells or airway therapeutics of the present invention can be used to treat a range of pulmonary conditions. Such conditions include pulmonary hypertension, neonatal pulmonary hypertension, neonatal bronchopulmonary dysplasia, chronic obstructive pulmonary disease (COPD), acute and chronic bronchitis, emphysema, bronchiolitis, bronchiectasis, radiation pneumonitis, hypersensitivity, pneumonitis, acute inflammatory asthma, acute smoke inhalation, thermal lung injury, allergic asthma, iatrogenic asthma, cystic fibrosis, and alveolar proteinosis, alpha-1-protease deficiency, pulmonary inflammatory disorders, pneumonia, acute respiratory distress syndrome, acute lung injury, idiopathic respiratory distress syndrome, and idiopathic pulmonary fibrosis.

In certain embodiments, compositions of the present invention which may include stem cells and/or airway therapeutics can be used as part of methods for treating pulmonary inflammation. Examples of pulmonary inflammation that can be treated include those associated with pulmonary hypertension, neonatal pulmonary hypertension, neonatal bronchopulmonary dysplasia, chronic obstructive pulmonary disease, acute bronchitis, chronic bronchitis, emphysema, bronchiolitis, bronchiectasis, radiation pneumonitis, hypersensitivity, pneumonitis, acute inflammatory asthma, acute smoke inhalation, thermal lung injury, allergic asthma, iatrogenic asthma, cystic fibrosis, alveolar proteinosis, alpha-1-protease deficiency, pulmonary inflammatory disorders, pneumonia, acute respiratory distress syndrome, acute lung injury, idiopathic respiratory distress syndrome, or idiopathic pulmonary fibrosis.

For instance, the present invention provides a method for causing lung regeneration in a subject in need thereof comprising administering to subject an effective amount of DASCs to the subject.

In certain embodiments, the subject is a mammal. In a preferred embodiment, the mammal is human.

In certain embodiments, the subject suffers from acute airway disease, lung fibrosis or degenerative upper airway disease. In other embodiments, the administration of DASCs treats acute airway disease, lung fibrosis or degenerative upper airway disease.

The disclosure further provides a use of the stem cells and/or airway therapeutics in the manufacture of a medicament for promoting lung tissue regeneration or preventing or slowing lung tissue degeneration.

The disclosure further provides a composition of purified airway epithelial stem cells, which cells are keratin 5 (Krt5) positive and p63 positive, can propagate for at least 10 doublings, and more preferably at least 20, 30, 40, 50 or even 60 doublings, while maintaining a pluripotent phenotype, and can differentiate into airway epithelia. In certain embodiments, the composition includes a clonal population of airway epithelial stem cells. The airway epithelial stem cells can be nasal epithelial stem cells (NESCs) (i.e., isolated from nasal turbinate); trachael airway stem cells (TASCs) (i.e., isolated from tracheobronchial epithelia); or distal airway stem cell (DASC) (i.e., isolated from isolated from distal airway tissue). In certain embodiments, the airway epithelial stem cells are mammalian cells. The airway stem epithelial cells can be human cells.

The disclosure further provides a method of screening for an agent which may be used to cause lung regeneration and/or prevent degeneration, including the steps of providing airway epithelial stem cells, which cells are keratin 5 (Krt5) positive and p63 positive, can propagate for at least 10 doublings, and more preferably at least 20, 30, 40, 50 or even 60 doublings, while maintaining a pluripotent phenotype, and can differentiate into airway epithelia; contacting the airway epithelial stem cells with a test agent; and detecting the ability of the test agent to increase viability, growth, migration or differentiation of the airway epithelial stem cells, and/or increased secretion of paracrine factors able to prevent IL-3 mediated inflammation and/or remodeling of lung tissue. Wherein if the test agent increases viability, growth, migration, differentiation and/or paracrine secretion of the airway epithelial stem cells than the test agent may be effective in causing lung regeneration.

In certain embodiments, the airway epithelial stem cells are distal airway stem cell (DASC) isolated from isolated from distal airway tissue. In other embodiments, the test agent is also contacted with normal cells or tissue of the lung, and the differential ability, if any, of the test agent to increase the viability, growth, migration or differentiation of the normal cells or tissue is compared to that with the airway epithelial stem cells. In other embodiments, the airway epithelial stem cells are human cells. In other embodiments, the test agent is selected for further drug development if the test increases the viability, growth or ability to differentiation of the airway epithelial stem cells by at least 20%.

In certain embodiments, the airway epithelial stem cells are provided as a clonal population of cells. In other embodiments the test agent is small molecule, carbohydrate, peptide or nucleic acid. The test agent can specifically bind to a cell surface protein on the clonal population of cells. The test agent can also be an antibody or antibody mimetic.

The disclosure further provides a method for causing lung regeneration in a subject in need thereof comprising administering to the subject an effective amount of the medicament described above to the subject to promote lung regeneration in the subject. The subject can be a mammal. That mammal can be a human. In certain embodiments, the subject suffers from acute airway disease, lung fibrosis or degenerative upper airway disease. In other embodiments, the administration of airway epithelial stem cells treats acute airway disease, lung fibrosis or degenerative upper airway disease.

In one aspect, the disclosure provides a method for causing lung regeneration, comprising administering to a subject a therapeutic amount of an agent that increases the expression and/or biological activity of one or more of the Cluster B genes set forth in FIG. 14 or 15, such that the lung is regenerated.

In another aspect, the disclosure provides a method of identifying a compound useful for regenerating lung tissue, the method comprising administering a test compound to an H1N1 infected mouse and determining the amount of epithelial metaplasia in the presence and absence of the test compound, wherein an increase in the amount of distal airway stem cells (DASCs) identifies a compound useful for regenerating lung tissue.

The disclosure further provides a method for causing lung regeneration in a subject in need thereof comprising administering to the subject an effective amount of one or more proteins, or active fragments thereof, secreted by airway epithelial stem cells, thereby treating or preventing acute airway disease, lung fibrosis or degenerative upper airway disease in the subject. The subject can be a mammal. That mammal can be a human. In certain embodiments, the subject suffers from acute airway disease, lung fibrosis or degenerative upper airway disease.

The disclosure further provides a method of screening for an agent to promote lung regeneration. The method includes the steps of providing a mammal; administering an agent (such as an EGFR inhibitor and lipopolysaccharide (LPS)), thereby inducing symptoms associated with acute lung injury (ALI) in the mammal; and administering the agent to the mammal with induced ALI; wherein if the test agent improves the symptoms associated with ALI then the test agent may be effective in causing lung regeneration.

In certain embodiments, the mammal is a rodent. Specifically the rodent can be a mouse, rat or rabbit. In certain embodiments, the EGFR inhibitor is giftinib. In other embodiments, the EGFR inhibitor is administered daily. Specifically, the EGFR inhibitor can be administered for three days. In certain embodiments, the LPS is administered at between 150 and 300 µg per day. Specifically, the LPS can be administered for three days.

In another embodiment, fibrosis is induced in the mammal prior to administering EGFR inhibitor and lipopolysaccharide (LPS) to the mammal. This fibrosis can be induced by administering bleomycin. The bleomycin can be administered intratracheally or intraperitoneally.

The disclosure also provides a method of isolating a population of stem cells. The method includes the steps of providing a sample of nasal, tracheal or lung tissue; washing the tissue in washing medium; dissociating cells from the tissue; washing the cells in washing medium; resuspending the cells in growth media; filtering the cells; and plating the cells on lethally irradiated 3T3-J2 fibroblasts.

In certain embodiments, the cold washing medium comprises Dulbecco's modified Eagle's medium (DMEM). In other embodiments, the tissue is dissociated by cutting the tissue into pieces and digesting the pieces in digestion medium. The digestion medium comprises DMEM, 5% fetal bovine serum and 2 mg/ml collagenase. In other embodiments, the growth medium comprises 5 mg/ml insulin, 10 ng/ml EGF, $2 \times 10^{-9}$ M 3,3',5-triiodo-L-thyronine, 0.4 mg/ml hydrocortisone, 24 mg/ml adenine, $1 \times 10^{-10}$ M cholera toxin in DMEM/Ham's F12 3:1 medium with 10% fetal bovine serum. In other embodiments, the filtering is performed by passing the cells through 70 µm nylon cell strainer.

The disclosure also provides a method of treating chronic obstructive pulmonary disease (COPD) or idiopathic pulmonary fibrosis (IPF) in a subject in need thereof comprising inducing acute lung injury (ALI) in the subject, thereby treating COPD or IPF by inducing acute injury which promotes activation of regenerative responses from lung stem cells. In certain embodiments, the ALI is induced by delivery of one or more inflammatory agents. The delivery can be systemic or localized. In other embodiments, the inflammatory agents are selected from lipopolysaccharide (LPS), EGFR inhibitors, TNF-α, IL-1a, IL-1b, IL-6, IL-8, and highly controlled bacterial strains (HCBS). The EGFR inhibitor can be gefitinib or erlotinib.

In another embodiment, the method of treating chronic obstructive pulmonary disease (COPD) or idiopathic pulmonary fibrosis (IPF), also includes administering an ablative technology to the subject. In certain embodiments, the ablative technology is radiofrequency ablation (RFA), photodynamic therapy or cryoablation.

In another embodiment, the method of treating chronic obstructive pulmonary disease (COPD) or idiopathic pulmonary fibrosis (IPF), also includes administering airway adult stem cells to the subject after, during or before induction of ALI. The stem cells can be exogenously grown. The stem cells can also be allogenic or autologous to the subject. The stem cells can also be TASCs or DASCs. The stem cells can also be isolated from biopsies of the upper and lower airways via bronchoscopy.

BRIEF DESCRIPTION OF THE DRAWINGS

FIG. 11 is a table listing differentially expressed genes between TASC and DASC stem cell pedigrees.

FIG. 15 is a table listing genes from the analysis of gene clusters A-D.

DETAILED DESCRIPTION

I. Overview

Figure 1:
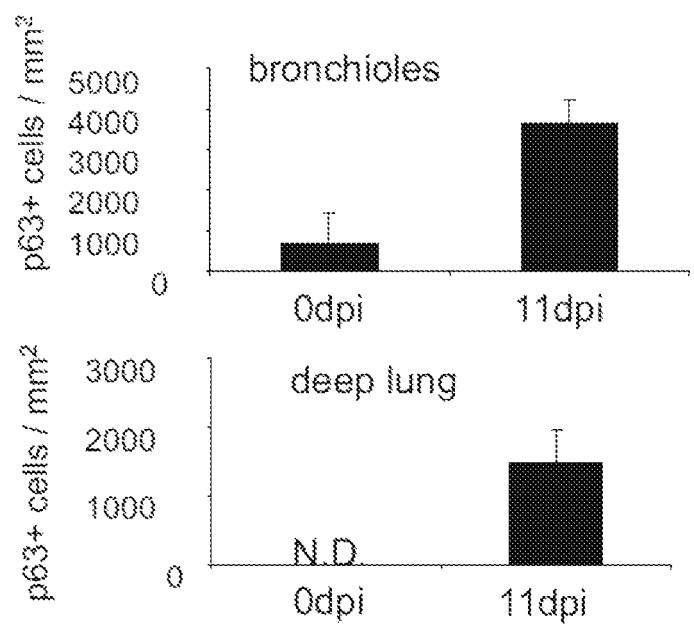
FIG. 1 shows p63-expressing basal cells in the bronchioles versus deep lung of normal mice at 0 and 11 dpi.

The present disclosure shows the induction and recovery from an acute respiratory distress-like syndrome in mice infected with sublethal doses of a murine-adapted H1N1 influenza virus. The disclosure shows that despite extensive damage to airway epithelial tissues, a p63-expressing population of cells in bronchioles undergoes a massive expansion and dispersion to sites of affected lung parenchyma. These migratory p63-expressing cells form discrete foci or "pods" that expand to a size and shape approximating those of alveoli and express genes linked to alveolar function. In parallel studies, three regiospecific stem cells were cloned from human airways demonstrate that one of these, the distal airway stem cell (DASC), has the unique potential of differentiating to alveolar lineages. These p63-expressing cells participate in alveolar assembly processes modeled by human DASCs in vitro, and therefore represent key features in lung regeneration in response to acute respiratory distress syndrome (ARDS).

Recovery from lung damage that has advanced to ARDS is highly variable and poorly understood at present. Critical questions remain to understand the differential fates of ARDS patients, the potential of lung regeneration versus fibrosis, and whether therapies can sway clinical outcomes. This disclosure addresses the recovery from ARDS in mice infected by H1N1 influenza. The histological evidence suggests a largely complete lung restoration several months following severe influenza infection (this study; Narasaraju et al., 2009). In fact the disclosure shows that, unlike bleomycin-induced ARDS, which invariably leads to fibrosis without evidence of regeneration (Moore and Hogaboam, 2008; Hoshino et al., 2009), mice recovering from influenza infections lack detectable lung fibrosis even following viral doses approaching the LD50. These data suggest that considerable regeneration of lung tissue, including complex alveolar-capillary networks, must be acting in this recovery. Indeed for the conducting, upper airways of mice, such as nasal passages, trachea, and bronchi, there are abundant data for regeneration after severe damage involving p63-expressing basal cells (Stripp and Reynolds, 2008; Rock et al., 2010). Despite this progress in understanding stem cells of the conducting airways, definitive evidence for a stem cell that can contribute to lung regeneration has been more elusive. Bronchioalveolar stem cells, or BASCs (Kim et al., 2005), have been a useful model for such stem cells but have not been cloned nor characterized beyond a limited marker set. More recently, a c-Kit-positive stem cell from the human airways expressing many markers of embryonic stem (ES) cells has been described to give rise to both epithelial and endothelial components of alveolar capillary complexes in xenograft experiments (Kajstura et al., 2011). The stem cells described herein, are fundamentally different from BASCs or the c-Kit, ES-like stem cells presented earlier and first drew attention as massive numbers of p63-expressing cells in the damaged lung parenchyma at the height of influenza-induced damage. p63-expressing cells are not found in normal interstitial lung, and rarely even detected in normal bronchioles. However, p63 cells increase dramatically in bronchioles in the first several days of influenza infection, and appear in nearby damaged interstitial lung at 11 days post infection where they continue proliferation and assemble into pods. Remarkably, the number of clonogenic p63-expressing cells in the distal airways increases several hundred-fold within seven days of influenza infection, and these cells assume aspects of gene expression patterns seen in p63-expressing stem cells in the epidermis during wound repair. Pods containing these cells are almost always found in a radial pattern about a bronchiole that also has p63-expressing cells, and not about bronchioles that lack p63 cells. One interpretation of these data is that bronchioles are the source of these cells, a concept supported by lineage tracing experiments with the Krt14-Cre/Rosa26-stop-LacZ mice.

The efforts to clone and characterize three regiospecific stem cells of the airways has provided a foundation for understanding the nature of the p63-expressing cells that comprise the Krt5 pods following influenza infection. The role of p63-expressing basal cells as stem cells for distal lung was largely discounted because they proved to be rare in the small bronchioles compared with the upper airways. Thus the ease by which immature clones could be generated of p63-expressing cells from populations of human distal airway epithelial cells was surprising. Despite the nearly 99% overlap in gene expression between DASCs and the upper airway TASCs and NESCs, DASCs displayed commitment to a unique program of differentiation that includes alveolar epithelium.

These Krt5 pods are intermediates in alveolar regeneration of influenza-damaged lung, and not a pathogenic pathway akin to bronchiectasis. 11 dpi Krt5 pods are solid spheres of cells that develop lumen and expand in size over the next 10 days to form alveoli-like structures. This hollowing and unilaminar appearance is strikingly similar in timing and appearance to the alveoli-like structures formed by human DASCs in 3-D cultures. These data were further supported by the co-staining of the Krt5 pods with antibodies directed to antigens found exclusively in alveoli such as PDPN and the target of the 11B6 monoclonal antibody. Neither of these antibodies reacts with regions of influenza-damaged lung that lack Krt5 pods.

Perhaps the most intriguing evidence favoring a role for Krt5 pods in alveolar regeneration was the direct comparison of gene expression profiles of discrete regions of lung at 25 dpi. Four regions are evident in these lungs: 1) normal lung marked by ordered alveolar networks, 2) highly infiltrated zones without alveolar markers whatsoever, 3) zones of immune cell infiltration and disordered SPC staining, and 4) clusters of Krt5 pods showing intermediate infiltration. The expression microarray data revealed that the high-density regions (SPC+ or SPC−) showed similar patterns of gene expression marked by inflammation, innate immune functions, and B and T cell profiles. From these data, which are consistent with the high level of infiltration of both regions and the very low expression of alveolar markers such as PDPN or the 11B6 monoclonal antibody, it is likely that both regions are damaged and not undergoing active repair. Regions marked by clusters of Krt5 pods, in contrast, had gene expression profiles that showed significant overlap with those of normal regions of interstitial lung. Within the set of genes overlapping between the clusters of Krt5 pods and the normal lung were genes common to AT1 cells. Interestingly, Gene Ontology analysis showed that these overlapping genes contained genes involved in angiogenesis, endothelin signaling, and aromatic amine degradation, all processes or functions attributed to lung endothelial cells and the formation of new blood vessels. Thus regions occupied by Krt5 pods are likely associated with, in addition to AT1 cell markers, the initiation of new blood vessels. It is tempting to speculate that such angiogenesis is related to the need to bring capillary beds into direct contact with regenerating alveolar structures.

II. Definitions

The term "agent" includes any substance, molecule, element, compound, entity, or a combination thereof. It includes, but is not limited to, e.g., protein, oligopeptide, small organic molecule, polysaccharide, polynucleotide, and the like. It can be a natural product, a synthetic compound, or a chemical compound, or a combination of two or more substances As used herein, the term "RNAi agent" refers to an agent, such as a nucleic acid molecule, that mediates gene-silencing by RNA interference, including, without limitation, small interfering siRNAs, small hairpin RNA (shRNA), and microRNA (miRNA).

The term "cell surface receptor ligand", as used herein, refers to any natural ligand for a cell surface receptor.

The term "antibody" encompasses any antibody (both polyclonal and monoclonal), or fragment thereof, from any animal species. Suitable antibody fragments include, without limitation, single chain antibodies (see e.g., Bird et alt (1988) Science 242:423-426; and Huston et at (1988) Proc. Natl. Acad. Sci. U.S.A 85:5879-5883, each of which is herein incorporated by reference in its entirety), domain antibodies (see, e.g., U.S. Pat. Nos. 6,291,158; 6,582,915; 6,593,081; 6,172,197; 6,696,245, each of which is herein incorporated by reference in its entirety), Nanobodies (see, e.g., U.S. Pat. No. 6,765,087, which is herein incorporated by reference in its entirety), and UniBodies (see, e.g., WO2007/059782, which is herein incorporated by reference in its entirety The term "antibody-like molecule", as used herein, refers to a non-immunoglobulin protein that has been engineered to bind to a desired antigen. Examples of antibody-like molecules include, without limitation, Adnectins (see, e.g., WO 2009/083804, which is herein incorporated by reference in its entirety), Affibodies (see, e.g., U.S. Pat. No. 5,831,012, which is herein incorporated by reference in its entirety), DARPins (see, e.g., U.S. Patent Application Publication No. 2004/0132028, which is herein incorporated by reference in its entirety), Anticalins (see, e.g., U.S. Pat. No. 7,250,297, which is herein incorporated by reference in its entirety), Avimers (see, e.g., U.S. Patent Application Publication Nos. 200610286603, which is herein incorporated by reference in its entirety), and Versabodies (see, e.g., U.S. Patent Application Publication No. 2007/0191272, which is hereby incorporated by reference in its entirety).

The term "biological activity" of a gene, as used herein, refers to a functional activity of the gene or its protein product in a biological system, e.g., enzymatic activity and transcriptional activity.

The term "biocompatible delivery vehicle", as used herein, refers to any phyioslogically compatible compound that can carry a drug payload, including, without limitation, microcapsules, microparticles, nanoparticles, and liposomes.

The term "suitable control", as used herein, refers to a measured mRNA or protein level (e.g. from a tissue sample not subject to treatment by an agent), or a reference value that has previously been established.

The term "pluripotent" as used herein, refers to a stem or progenitor cell that is capable of differentiating into any of the three germ layers endoderm, mesoderm or ectoderm.

The term "multipotent", as used herein, refers to a stem or progenitor cell that is capable of differentiating into multiple lineages, but not all lineages. Often, multipotent cells can differentiate into most of the cells of a particular lineage, for example, hematopoietic stem cells.

The term "oligopotent", as used herein, refers to a stem or progenitor cell that can differentiate into two to five cell types, for example, lymphoid or myeloid stem cells.

The term "positive", as used herein, refers to the expression of an mRNA or protein in a cell, wherein the expression is at least 5 percent of the expression of actin in the cell.

The term "negative", as used herein, refers to the expression of an mRNA or protein in a cell, wherein the expression is less than 1 percent of the expression of actin in the cell.

"Pulmonary administration" refers to any mode of administration that delivers a pharmaceutically active substance to any surface of the lung. The modes of delivery can include, but are not limited to, those suitable for endotracheal administration, i.e., generally as a liquid suspension instillate, as a dry powder "dust" or insufflate, or as an aerosol. Pulmonary administration can be utilized for both local and systemic delivery of pharmaceutically active substances.

"Active agent" refers to a therapeutic or diagnostic compound that is administered to achieve a desired therapeutic or diagnostic result or purpose. Pharmaceutically active agent refers to an agent that is a biologically-active synthetic or natural substance that is useful for treating a medical or veterinary disorder or trauma, preventing a medical or veterinary disorder, or regulating the physiology of a human being or animal. The range of active compounds is considered below.

III. Exemplary Embodiments

A. Molecular Signature of Regenerating Lung Cells

Transcriptome analysis of RNA derived from a population of cells in regenerating lung led to the remarkable discovery that these cells have a distinct molecular signature. In particular, a number of genes were identified as being upregulated in these cells. Moreover, a subset of these genes (set forth below in Table 1, the sequences of which are each specifically incorporated herein by reference to their respective RefSeq Transcript ID numbers) include secreted proteins that are necessary for the process of regeneration to occur in lung. In certain embodiments, these secreted proteins are used as therapeutics to induce lung regeneration. Table 1 also includes genes that are membrane receptors that are necessary for the process of regeneration to occur in the lung. In certain embodiments, modulators of these membrane receptors are used as therapeutics to induce lung regeneration. Accordingly, the present invention makes use of the identified genes to provide methods and compositions for diagnosing, monitoring or causing lung regeneration. However, it should be appreciated that such methods and compositions are not limited to diagnosing, monitoring or causing lung regeneration, but can be can be used more generally for diagnosing, monitoring or treating or preventing any disease arising from lung pathology. Such diseases include, without limitation, acute airway disease, influenza, lung fibrosis or degenerative upper airway disease.

TABLE I

| Gene Symbol | RefSeq | p-value (Attribute) | K5 pod vs. Normal Alveoli |
|---|---|---|---|
| Plunc | NM_011126 | 0.00012616 | 113.668 |
| Scgb3a1 | NM_170727 | 1.47E-07 | 106.77 |
| Gpx2 | NM_030677 | 1.50E-05 | 100.758 |
| Ltf | NM_008522 | 5.72E-06 | 64.8327 |
| Scgb3a2 | NM_054038 | 0.0001064 | 53.5997 |
| Cyp2f2 | NM_007817 | 0.00143717 | 25.7893 |
| Gabrp | NM_146017 | 1.66E-08 | 21.3639 |
| Fmo3 | NM_008030 | 0.00150149 | 18.3757 |
| Retnla | NM_020509 | 0.00163579 | 13.5759 |
| Reg3g | NM_011260 | 1.21E-05 | 13.4839 |
| Gsto1 | NM_010362 | 8.59E-07 | 12.7842 |
| Pon1 | NM_011134 | 0.00855739 | 12.4008 |
| Cp | NM_001042611 | 7.60E-06 | 10.8719 |
| Agr2 | NM_011783 | 6.61E-06 | 9.22423 |
| Tff2 | NM_009363 | 7.14E-05 | 8.85996 |
| Trf | NM_133977 | 6.35E-06 | 8.67283 |
| Adh7 | NM_009626 | 0.00024095 | 8.59695 |
| Sult1d1 | NM_016771 | 0.0150136 | 7.64619 |
| Pglyrp1 | NM_009402 | 5.18E-05 | 7.58559 |
| Sox2 | NM_011443 | 1.98E-07 | 7.50424 |
| Cxcl17 | NM_153576 | 3.67E-05 | 6.35427 |
| Saa3 | NM_011315 | 4.50E-05 | 5.93148 |
| Ehf | NM_007914 | 2.73E-05 | 5.26746 |
| Krt15 | NM_008469 | 0.00029253 | 5.2583 |
| Dmbt1 | NM_007769 | 3.61E-06 | 5.21175 |
| U46068 | NM_001012392 | 6.58E-06 | 5.01759 |
| Muc5b | NM_028801 | 2.74E-06 | 4.95243 |
| AA467197 | ENSMUST00000110512 | 0.00123857 | 4.89692 |
| Lilrb4 | NM_013532 | 0.0173497 | 4.81361 |
| Adam28 | NM_010082 | 2.85E-05 | 4.79275 |
| Fxyd3 | NM_008557 | 4.82E-06 | 4.77983 |
| Sprr1a | NM_009264 | 0.00031819 | 4.77646 |
| S100a8 | NM_013650 | 0.00106991 | 4.57395 |
| S100a9 | NM_009114 | 0.0146528 | 4.09731 |
| Anxa8 | NM_013473 | 0.00052158 | 3.94476 |
| Rsph1 | NM_025290 | 0.00233354 | 3.77745 |
| Pigr | NM_011082 | 8.13E-07 | 3.75144 |
| Msln | NM_018857 | 6.02E-06 | 3.61261 |
| Gstm2 | NM_008183 | 0.00193389 | 3.51555 |
| Chad | NM_007689 | 0.00011957 | 3.47697 |
| Sfn | NM_018754 | 0.0217617 | 3.40115 |
| Krt5 | NM_027011 | 3.74E-05 | 3.19306 |
| C3 | NM_009778 | 0.00331331 | 3.14915 |
| F3 | NM_010171 | 0.00624646 | 3.07399 |
| Krt14 | NM_016958 | 7.35E-06 | 3.0048 |
| Clca3 | NM_017474 | 0.0176591 | 2.96908 |
| 1700016K19Rik | NM_198637 | 0.00456716 | 2.95062 |
| Gp2 | NM_025989 | 0.0105723 | 2.89296 |
| Casp4 | NM_007609 | 0.0127789 | 2.87907 |
| Perp | NM_022032 | 0.00192193 | 2.86531 |
| Clic6 | NM_172469 | 0.00470743 | 2.85849 |
| Mt2 | NM_008630 | 0.0202544 | 2.81027 |
| Acsm1 | NM_054094 | 0.00022724 | 2.80491 |
| Gdpd2 | NM_023608 | 0.00010237 | 2.79524 |
| Meig1 | NM_008579 | 0.00036579 | 2.76759 |
| Cfb | NM_008198 | 0.0023459 | 2.76559 |
| Defb1 | NM_007843 | 0.0221173 | 2.74333 |
| Clec4d | NM_010819 | 0.00042434 | 2.74123 |
| Slc15a2 | NM_021301 | 0.00282514 | 2.73702 |
| Fetub | NM_021564 | 0.00067677 | 2.72546 |
| Dnali1 | NM_175223 | 0.00151708 | 2.69165 |

TABLE I-continued

| Gene Symbol | RefSeq | p-value (Attribute) | K5 pod vs. Normal Alveoli |
|---|---|---|---|
| Fabp6 | NM_008375 | 0.0154033 | 2.6901 |
| D17H6S56E-5 | L78788 | 0.00118662 | 2.67613 |
| Lrrc23 | NM_013588 | 0.00939528 | 2.64403 |
| Rbp4 | NM_001159487 | 0.00631239 | 2.62326 |
| Acsl1 | NM_007981 | 0.0160217 | 2.54696 |
| Cd14 | NM_009841 | 0.00563995 | 2.5195 |
| Tmem176b | NM_023056 | 0.0116429 | 2.51414 |
| Itln1 | NM_010584 | 0.00053001 | 2.51055 |
| Glu1 | NM_008131 | 0.0007032 | 2.50236 |
| Nhp2 | NM_026631 | 0.00208786 | 2.45884 |
| Selenbp2 | NM_019414 | 0.00033742 | 2.45414 |
| Tanc2 | NM_181071 | 0.040937 | 2.4326 |
| 1700009P17Rik | BC061017 | 0.0209657 | 2.41307 |
| Qsox1 | NM_001024945 | 0.00025577 | 2.35964 |
| Lrrc26 | NM_146117 | 0.0023331 | 2.35447 |
| Mettl5 | NM_029280 | 0.00457277 | 2.33763 |
| Alas1 | NM_020559 | 0.00040073 | 2.30736 |
| B3galt2 | NM_020025 | 0.0438602 | 2.27493 |
| Vtcn1 | NM_178594 | 0.00039493 | 2.26372 |
| 5430414B19Rik | AK017307 | 0.00197445 | 2.24221 |
| D930014E17Rik | NM_020616 | 0.00164731 | 2.23616 |
| Ptn | NM_008973 | 0.00036677 | 2.21477 |
| H2-K1 | NM_001001892 | 0.0465364 | 2.20058 |
| Enkur | NM_027728 | 0.0189993 | 2.18733 |
| Msc | NM_010827 | 0.00188297 | 2.14558 |
| Clca2 | NM_030601 | 0.00097237 | 2.12828 |
| Trp63 | NM_001127259 | 0.0117549 | 2.10084 |
| Mall | NM_145532 | 0.00531499 | 2.09598 |
| Pla2g16 | NM_139269 | 0.0193712 | 2.07677 |
| Por | NM_008898 | 5.91E-06 | 2.05223 |
| Fam107b | BC021353 | 0.00210472 | 2.04837 |
| Prom1 | NM_008935 | 0.00017192 | 2.04515 |
| Es22 | NM_133660 | 0.0313909 | 2.03637 |
| Tspan1 | NM_133681 | 0.0155271 | 2.0329 |
| Muc4 | NM_080457 | 0.0003253 | 2.0208 |
| Ccdc113 | NM_172914 | 0.00134217 | 2.01754 |
| Kif21a | NM_001109040 | 1.41E-05 | 1.9939 |
| Aqp4 | NM_009700 | 0.00113622 | 1.99302 |
| Gnb2l1 | NM_008143 | 0.0332985 | 1.98609 |
| Ccdc67 | NM_181816 | 0.00024309 | 1.98408 |
| Samd9l | NM_010156 | 0.0312697 | 1.97645 |
| Slc38a1 | NM_134086 | 0.00308758 | 1.97342 |
| Cd24a | NM_009846 | 0.0212141 | 1.96957 |
| Bmpr1b | NM_007560 | 0.00388449 | 1.96222 |
| Rtp4 | NM_023386 | 0.0154499 | 1.95804 |
| AU018778 | BC013479 | 0.00928803 | 1.95019 |
| Pdcd4 | NM_011050 | 0.0151617 | 1.94712 |
| Mgat4a | NM_173870 | 0.00739108 | 1.9402 |
| Morn2 | NM_194269 | 0.00236872 | 1.93797 |
| Ckmt1 | NM_009897 | 1.82E-05 | 1.93425 |
| Ntf3 | NM_008742 | 0.0185808 | 1.91891 |
| Six1 | NM_009189 | 0.00403635 | 1.91332 |
| Slc16a11 | NM_153081 | 0.0215385 | 1.90656 |
| Il13ra1 | NM_133990 | 0.0144604 | 1.89466 |
| Ikzf2 | NM_011770 | 0.00151251 | 1.89228 |
| Alox15 | NM_009660 | 0.00017256 | 1.88783 |
| Il1f9 | NM_153511 | 0.0448469 | 1.88738 |
| Dclk1 | NM_019978 | 0.00914774 | 1.88537 |
| Fam154b | NM_177894 | 0.0356182 | 1.88163 |
| Nfil3 | NM_017373 | 0.0355677 | 1.87874 |
| Slco1a5 | NM_130861 | 0.00573739 | 1.87694 |
| Rassf9 | NM_146240 | 0.00187781 | 1.86697 |
| Gmnn | NM_020567 | 0.046648 | 1.85493 |
| Clca4 | NM_139148 | 0.0210313 | 1.85155 |
| Oit1 | NM_146050 | 0.00522638 | 1.8498 |
| Nupr1 | NM_019738 | 0.0116456 | 1.84107 |
| Steap1 | NM_027399 | 0.00628025 | 1.83493 |
| Epcam | NM_008532 | 0.0253575 | 1.8325 |
| Aldoc | NM_009657 | 0.00184216 | 1.83016 |
| Nfe2l3 | NM_010903 | 0.00088926 | 1.81016 |
| Aspa | NM_023113 | 0.00452845 | 1.80294 |
| Il1b | NM_008361 | 0.027142 | 1.80157 |
| Gtsf1l | NM_026630 | 0.041179 | 1.78592 |
| Foxa1 | NM_008259 | 0.00028249 | 1.7639 |
| Cd44 | NM_009851 | 0.0416809 | 1.75812 |
| Cldn10 | NM_023878 | 0.00253158 | 1.74988 |
| Cmtm7 | NM_133978 | 0.0430916 | 1.74925 |
| Polr3d | NM_025945 | 0.01405 | 1.747 |
| Gjb2 | NM_008125 | 0.00026718 | 1.74041 |
| Bhlhe40 | NM_011498 | 0.0120946 | 1.73441 |
| Cyp4a12a | NM_177406 | 0.036461 | 1.73394 |
| Pla2g4a | NM_008869 | 0.00241126 | 1.73378 |
| Ankrd37 | NM_001039562 | 0.00707205 | 1.73327 |
| Rdh10 | NM_133832 | 0.00303255 | 1.73033 |
| Xrcc6 | NM_010247 | 0.0290776 | 1.72768 |
| Olfr120 | NM_146631 | 0.0447063 | 1.71614 |
| 9530008L14Rik | NM_175417 | 0.0185805 | 1.71367 |
| Mki67ip | NM_026472 | 0.019014 | 1.71259 |
| Sap30 | NM_021788 | 0.0379029 | 1.70855 |
| Ctrl | NM_007620 | 0.0224507 | 1.70659 |
| Myb | NM_010848 | 0.0418231 | 1.7029 |
| Krt17 | NM_010663 | 0.00420656 | 1.70231 |
| Serpinb5 | NM_009257 | 0.00889648 | 1.6925 |
| Kcne3 | NM_020574 | 0.0449453 | 1.68684 |
| Gcnt1 | NM_173442 | 0.0419343 | 1.67996 |
| Olfr47 | NM_146370 | 0.00311092 | 1.67905 |
| Rassf10 | NM_175279 | 0.0191312 | 1.67684 |
| Iqcg | NM_178378 | 0.0102771 | 1.66885 |
| Timp1 | NM_001044384 | 0.0464415 | 1.66132 |
| Slc27a2 | NM_011978 | 0.0349493 | 1.65621 |
| Dnajc5b | NM_025489 | 0.00430989 | 1.65048 |
| Slc25a35 | NM_028048 | 0.033864 | 1.63882 |
| Sox21 | NM_177753 | 0.00651426 | 1.6365 |
| Slc44a4 | NM_023557 | 0.00033129 | 1.63189 |
| Ccdc96 | NM_025725 | 0.00081144 | 1.63111 |
| Pcgf6 | NM_027654 | 0.00528518 | 1.62706 |
| Cops3 | NM_011991 | 0.039739 | 1.62393 |
| Ncbp2 | NM_026554 | 0.00536334 | 1.62055 |
| Six4 | NM_011382 | 0.0108913 | 1.61138 |
| 2610209A20Rik | NM_026010 | 0.00813988 | 1.60863 |
| V1rb8 | NM_053229 | 0.0211859 | 1.60418 |
| Bbs5 | NM_028284 | 0.0237837 | 1.60095 |
| Adamdec1 | NM_021475 | 0.00359962 | 1.59967 |
| Efcab9 | NM_027031 | 0.0161707 | 1.59172 |
| Gpr39 | NM_027677 | 0.0102092 | 1.58828 |
| Lpcat2 | NM_173014 | 0.0199438 | 1.58733 |
| Olfr512 | NM_146724 | 0.0339644 | 1.57981 |
| Dsg2 | NM_007883 | 0.0308923 | 1.57249 |
| Sorbs2 | NM_172752 | 0.00101831 | 1.56979 |
| Sh3bgrl2 | NM_172507 | 0.0193835 | 1.56608 |
| Fatm84a | NM_029007 | 0.0253308 | 1.56562 |
| Gpr64 | NM_178712 | 0.00094614 | 1.56547 |
| Gal3st1 | NM_016922 | 0.0231608 | 1.56449 |
| Elf3 | NM_007921 | 0.0461634 | 1.56331 |
| Foxq1 | NM_008239 | 0.00940963 | 1.56031 |
| Mrgpre | NM_175534 | 0.0122359 | 1.55823 |
| Ppp2r2b | NM_027531 | 0.0121615 | 1.55808 |
| Lrrc6 | NM_019457 | 0.00830165 | 1.55562 |
| Klk10 | NM_133712 | 0.0215366 | 1.5552 |
| Klf5 | NM_009769 | 0.0011174 | 1.5454 |
| 0610009D07Rik | NM_025323 | 0.0102273 | 1.54359 |
| Fgfbp1 | NM_008009 | 0.00010754 | 1.54335 |
| Tas2r135 | NM_199159 | 0.0258732 | 1.54084 |
| 5730469M10Rik | BC056635 | 0.00567594 | 1.53125 |
| Pigy | NM_025574 | 0.0263899 | 1.5304 |
| Dsc2 | NM_013505 | 0.0167853 | 1.52773 |
| Cldn2 | NM_016675 | 0.00644748 | 1.52763 |
| Csl | NM_027945 | 0.0147931 | 1.5264 |
| Gramd3 | NM_026240 | 0.0195986 | 1.52333 |
| 1810046J19Kik | NM_025559 | 0.0102072 | 1.52314 |
| Lrrc48 | NM_029044 | 0.014039 | 1.52029 |
| Cep70 | NM_023873 | 0.00215257 | 1.51678 |
| Rnf128 | NM_023270 | 0.00381025 | 1.51365 |
| Anspc13 | NM_181394 | 0.0112705 | 1.51051 |
| Mobkl2b | NM_178061 | 0.00493035 | 1.51014 |
| S100a14 | NM_025393 | 0.0422869 | 1.50609 |
| Galnt4 | NM_015737 | 0.0157572 | 1.50482 |

B. Airway Therapeutics

Another aspect of the invention is based on the observations that DASCs can cause repair and/or remodeling of damaged lung tissue in a distal manner, indicating the role of one or more paracrine factors. When compared to NESCs and TASCs, DASCs had a profoundly increased potency for inducing tissue regeneration, further indicating that the secretion of relevant paracrine factor(s) were upregulated in the DASCs as compared to the other two stem cell populations. Accordingly, it is contemplated that the use of one or more therapeutic agents which are derived from the secreted proteins of the DASC population can be used to treat or prevent diseases and disorders involving airway tissue. A list of genes which are upregulated in DASCs is provided in Table 1 above. The examples below are provided for one of those proteins, PLUNC, but may equally apply to other proteins encoded by the genes referenced in Table 1 above.

In one embodiment, the therapeutic agent includes the secreted protein PLUNC (also referred to as secretory protein in upper respiratory tracts or SPURT), or an active fragment thereof. The human PLUNC cDNA codes for a leucine-rich protein of 256 amino acids (GenBank: AF214562.1) which is 72% identical to the murine protein. The full length human PLUNC protein has the following sequence:

```
                                              (SEQ ID NO: 1)
MFQTGGLIVFYGLLAQTMAQFGGLPVPLDQTLPLNVNPALPLSPTGLA

GSLTNALSNGLLSGGLLGILENLPLLDILKPGGGTSGGLLGGLLGKVT

SVIPGLNNIIDIKVTDPQLLELGLVQSPDGHRLYVTIPLGIKLQVNTP

LVGASLLRLAVKLDITAEILAVRDKQERIHLVLGDCTHSPGSLQISLL

DGLGPLPIQGLLDSLTGILNKVLPELVQGNVCPLVNEVLRGLDITLVH

DIVNMLIHGLQFVIKV
```

The PLUNC proteins of the invention also include functional portions or fragments. The length of the fragment is not critical as long as it substantially retains the biological activity of the polypeptide. The therapeutic agent can be the full length protein, or can be a fragment thereof, such as the leucine rich region ranging from L-24 to L-218, or any other fragment or analog thereof which is able to recapitulate the activity of PLUNC for inhibiting IL-13 induced damage in in vitro lung tissue assays. Other illustrative fragments comprise at least about 4, 6, 8, 10, 12, 15, 20, 25, 30, 35, 40, 45, 50, 75, 100, 150, 200, or more contiguous amino acids of a PLUNC protein. In other embodiments, the fragment comprises no more than about 200, 150, 100, 75, 50, 45, 40, 35, 30, 25, 20, 15, 12, 10, 8, 6, or 4 contiguous amino acids of a PLUNC protein. In one embodiment, the fragment comprises, consists essentially of, or consists of a sequence from about residue 20 to about residue 41 of human SPLUNC1, e.g., about residue 22 to about residue 39, or the corresponding sequence (e.g., the approximately 20 amino acids immediately after the signal peptide) from another PLUNC protein.

Likewise, those skilled in the art will appreciate that the present invention also encompasses fusion polypeptides (and polynucleotide sequences encoding the same) comprising a PLUNC protein (or a functional fragment thereof). For example, it may be useful to express the polypeptide (or functional fragment) as a fusion protein that can be recognized by a commercially available antibody (e.g., FLAG motifs) or as a fusion protein that can otherwise be more easily purified (e.g., by addition of a poly-His tail). Additionally, fusion proteins that enhance the stability of the polypeptide may be produced, e.g., fusion proteins comprising maltose binding protein (MBP) or glutathione-S-transferase. As another alternative, the fusion protein can comprise a reporter molecule. In other embodiments, the fusion protein can comprise a polypeptide that provides a function or activity that is the same as or different from the activity of the polypeptide, e.g., a targeting, binding, or enzymatic activity or function.

Likewise, it will be understood that the polypeptides specifically disclosed herein will typically tolerate substitutions in the amino acid sequence and substantially retain biological activity. To identify polypeptides of the invention other than those specifically disclosed herein, amino acid substitutions may be based on any characteristic known in the art, including the relative similarity or differences of the amino acid side-chain substituents, for example, their hydrophobicity, hydrophilicity, charge, size, and the like.

In identifying amino acid sequences encoding polypeptides other than those specifically disclosed herein, the hydropathic index of amino acids may be considered. The importance of the hydropathic amino acid index in conferring interactive biologic function on a protein is generally understood in the art (see, Kyte and Doolittle, J. Mol. Biol. 157:105 (1982)). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like.

Each amino acid has been assigned a hydropathic index on the basis of its hydrophobicity and charge characteristics (Kyte and Doolittle, id.), these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5). Accordingly, the hydropathic index of the amino acid (or amino acid sequence) may be considered when modifying the polypeptides specifically disclosed herein.

It is also understood in the art that the substitution of amino acids can be made on the basis of hydrophilicity. U.S. Pat. No. 4,554,101 states that the greatest local average hydrophilicity of a protein, as governed by the hydrophilicity of its adjacent amino acids, correlates with a biological property of the protein. As detailed in U.S. Pat. No. 4,554,101, the following hydrophilicity values have been assigned to amino acid residues: arginine (+3.0); lysine (.+~.3.0); aspartate (+3.0.+~.1); glutamate (+3.0.+~.1); serine (+0.3); asparagine (+0.2); glutamine (+0.2); glycine (0); threonine (−0.4); proline (−0.5.+~.1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4).

Thus, the hydrophilicity of the amino acid (or amino acid sequence) may be considered when identifying additional polypeptides beyond those specifically disclosed herein.

In embodiments of the invention, the polynucleotide encoding the PLUNC protein (or functional fragment) will hybridize to the nucleic acid sequences encoding PLUNC proteins that are known in the art or fragments thereof under standard conditions as known by those skilled in the art and encode a functional polypeptide or functional fragment thereof.

For example, hybridization of such sequences may be carried out under conditions of reduced stringency, medium stringency or even stringent conditions (e.g., conditions represented by a wash stringency of 35-40% formamide with 5×Denhardt's solution, 0.5% SDS and 1×SSPE at 37° C.; conditions represented by a wash stringency of 40-45% formamide with 5×Denhardt's solution, 0.5% SDS, and 1×SSPE at 42° C.; and conditions represented by a wash stringency of 50% formamide with 5×Denhardt's solution, 0.5% SDS and 1×SSPE at 42° C., respectively) to the polynucleotide sequences encoding the PLUNC protein or functional fragments thereof specifically disclosed herein. See, e.g., Sambrook et al., Molecular Cloning: A Laboratory Manual 2nd Ed. (Cold Spring Harbor, N.Y., 1989).

In other embodiments, polynucleotide sequences encoding the PLUNC protein have at least about 70%, 80%, 85%, 90%. 95%, 96%, 97%, 98%, 99% or higher sequence identity with the publicly known nucleic acid sequences (disclosed in GenBank) or functional fragments thereof and encode a functional polypeptide or functional fragment thereof.

Further, it will be appreciated by those skilled in the art that there can be variability in the polynucleotides that encode the polypeptides (and fragments thereof) of the present invention due to the degeneracy of the genetic code. The degeneracy of the genetic code, which allows different nucleic acid sequences to code for the same polypeptide, is well known in the literature Likewise, the polypeptides (and fragments thereof) of the invention include polypeptides that have at least about 70%. 80%, 85%, 90%. 95%, 96%, 97%, 98%. 99% or higher amino acid sequence identity with the publicly known polypeptide sequences.

As is known in the art, a number of different programs can be used to identify whether a polynucleotide or polypeptide has sequence identity or similarity to a known sequence. Sequence identity or similarity may be determined using standard techniques known in the art, including, but not limited to, the local sequence identity algorithm of Smith & Waterman, Adv. Appl. Math. 2:482 (1981), by the sequence identity alignment algorithm of Needleman & Wunsch, J. Mol. Biol. 48:443 (1970), by the search for similarity method of Pearson & Lipman, Proc. Natl. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Drive, Madison, Wis.), the Best Fit sequence program described by Devereux et al., Nucl. Acid Res. 12:387 (1984), preferably using the default settings, or by inspection.

An example of a useful algorithm is PILEUP. PILEUP creates a multiple sequence alignment from a group of related sequences using progressive, pairwise alignments. It can also plot a tree showing the clustering relationships used to create the alignment. PILEUP uses a simplification of the progressive alignment method of Feng & Doolittle, J. Mol. Evol. 35:351 (1987); the method is similar to that described by Higgins & Sharp, CABIOS 5:151 (1989).

Another example of a useful algorithm is the BLAST algorithm, described in Altschul et al., J. Mol. Biol. 215:403 (1990) and Karlin et al., Proc. Natl. Acad. Sci. USA 90:5873 (1993). A particularly useful BLAST program is the WU-BLAST-2 program which was obtained from Altschul et al., Meth. Enzymol., 266:460 (1996); blast.wustl/edu/blast/RE-ADME.html. WU-BLAST-2 uses several search parameters, which are preferably set to the default values. The parameters are dynamic values and are established by the program itself depending upon the composition of the particular sequence and composition of the particular database against which the sequence of interest is being searched, however, the values may be adjusted to increase sensitivity.

An additional useful algorithm is gapped BLAST as reported by Altschul et al., Nucleic Acids Res. 25:3389 (1997).

A percentage amino acid sequence identity value is determined by the number of matching identical residues divided by the total number of residues of the "longer" sequence in the aligned region. The "longer" sequence is the one having the most actual residues in the aligned region (gaps introduced by WU-Blast-2 to maximize the alignment score are ignored).

In a similar manner, percent nucleic acid sequence identity with respect to the coding sequence of the polypeptides disclosed herein is defined as the percentage of nucleotide residues in the candidate sequence that are identical with the nucleotides in the polynucleotide specifically disclosed herein.

The alignment may include the introduction of gaps in the sequences to be aligned. In addition, for sequences which contain either more or fewer amino acids than the polypeptides specifically disclosed herein, it is understood that in one embodiment, the percentage of sequence identity will be determined based on the number of identical amino acids in relation to the total number of amino acids. Thus, for example, sequence identity of sequences shorter than a sequence specifically disclosed herein, will be determined using the number of amino acids in the shorter sequence, in one embodiment. In percent identity calculations relative weight is not assigned to various manifestations of sequence variation, such as insertions, deletions, substitutions, etc.

In one embodiment, only identities are scored positively (+1) and all forms of sequence variation including gaps are assigned a value of "0," which obviates the need for a weighted scale or parameters as described below for sequence similarity calculations. Percent sequence identity can be calculated, for example, by dividing the number of matching identical residues by the total number of residues of the "shorter" sequence in the aligned region and multiplying by 100. The "longer" sequence is the one having the most actual residues in the aligned region.

In still other embodiments, the invention comprises treating or preventing damage to airway tissue using agents which upregulate the level of expression or secretion of protein shown in Table 1. To illustrate, TLR2 agonists such as Pam3CSK4 (a synthetic triacylated lipoprotein) and HKLM (heat-killed preparation of *Listeria monocytogenes*) can increase PLUNC expression. Synthetic small molecule agonists of TLR2 are also well known in the art, such as described in Guan et al. J Biol Chem. 2010 Jul. 30; 285(31): 23755-23762 and shown below. Accordingly, the invention contemplates the use of TLR2 agonists as therapeutic agents.

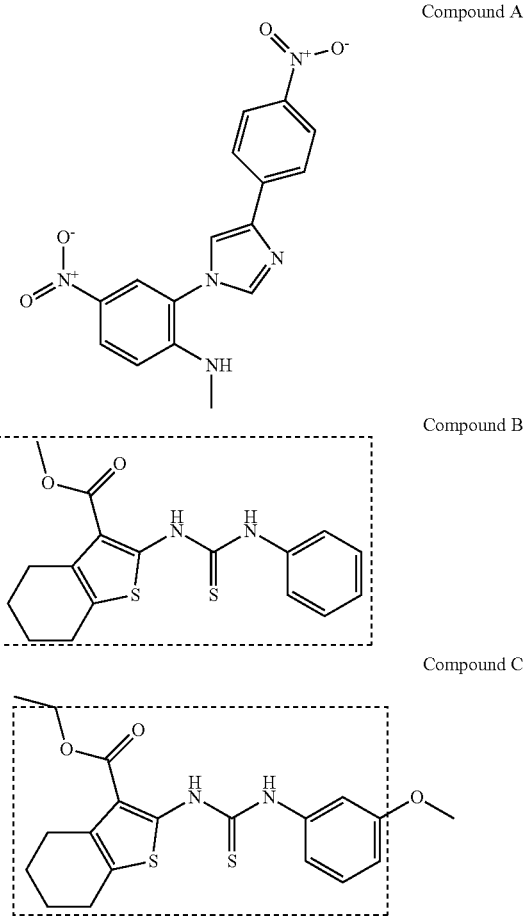

C. Formulation

The proteins, small molecules and other therapeutics of the invention may be formulated into a variety of acceptable compositions. Such pharmaceutical compositions can be administered to a mammalian host, such as a human patient, in a variety of forms adapted to the chosen route of administration, i.e., by lavage, orally or parenterally, by intravenous, intramuscular, pulmonary or inhalation routes. In certain preferred embodiments, the airway therapeutic agent is formulated for pulmonary delivery.

In cases where compounds, for example, the therapeutic agent is sufficiently basic or acidic to form stable nontoxic acid or base salts, administration of such compounds as salts may be appropriate. Examples of pharmaceutically acceptable salts are organic acid addition salts formed with acids that form a physiological acceptable anion, for example, tosylate, methanesulfonate, acetate, citrate, malonate, tartarate, succinate, benzoate, ascorbate, .alpha.-ketoglutarate, and .alpha.-glycerophosphate. Suitable inorganic salts may also be formed, including hydrochloride, sulfate, nitrate, bicarbonate, and carbonate salts. Pharmaceutically acceptable salts are obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids also are made.

Pharmaceutically acceptable salts of polypeptides include the acid addition salts (formed with the free amino groups of the polypeptide) that are formed with inorganic acids such as, for example, hydrochloric or phosphoric acids, or such organic acids as acetic, tartaric, mandelic and the like. Salts formed with the free carboxyl groups can also be derived from inorganic bases such as, for example, sodium, potassium, ammonium, calcium or ferric hydroxides, and such organic bases as isopropylamine, trimethylamine, 2-ethylamino ethanol histidine, procaine and the like.

Thus, the therapeutic agents of the present invention may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the compositions may be combined with one or more excipients and used in the form of ingestible tablets, buccal tablets, troches, capsules, elixirs, suspensions, syrups, wafers, and the like. Such compositions and preparations should contain at least 0.1% of active compound.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The therapeutic agents may also be administered intravenously or intraperitoneally by infusion or injection. Solutions of the active agents may be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient that are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the therapeutic agent(s) in the required amount in the appropriate solvent with various of the other ingredients, enumerated above, as required, followed by filter sterilization. In the case of sterile powders for the preparation of sterile injectable solutions, the preferred methods of preparation are vacuum drying and the freeze drying techniques, which yield a powder of the protease inhibitors, lipase inhibitors or antioxidants plus any additional desired ingredient present in the previously sterile-filtered solutions.

Useful dosages of airway therapeutics of the present invention can be determined by comparing in vitro activity, and in vivo activity in animal models. Methods for the extrapolation of effective dosages in mice, and other animals, to humans are known to the art; for example, see U.S. Pat. No. 4,938,949.

The amount of airway therapeutic agent, or active salts or derivatives thereof, required for use in treatment will vary not only with the particular salt selected but also with the route of administration, the nature of the condition being treated and the age and condition of the patient and will be ultimately at the discretion of the attendant physician or clinician.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator.

An airway therapeutic of the present invention can be delivered directly to the site of interest (the lung) to provide immediate relief of the symptoms of pulmonary inflammation. Such delivery can be by bronchoalveolar lavage, intratracheal administration, inhalation or bolus administration. In these case the surfactant mixture is included.

Procedures for performing pulmonary lavage are available in the art. See, e.g., U.S. Pat. No. 6,013,619. For example, pulmonary lavage can be performed as follows:

a) applying gas positive end-expiratory pressure (PEEP) with a ventilator into a lung section of the mammal at a regulated pressure, preferably from about 4 to 20 cm water;

b) instilling a lavage composition containing dilute surfactant in a pharmaceutically acceptable aqueous medium into one or more lobes or sections of the lung; and c) removing the resulting pulmonary fluid from the lung using short intervals of tracheo-bronchial suction, preferably using a negative pressure of about 20 to 100 mm mercury. Typically, the PEEP is applied for a preselected time period prior to instilling step (b), preferably up to about 30 minutes, and in addition PEEP is typically applied continuously during steps (b) and (c) and for a preselected time period after removing step (c), preferably up to about 6 hours.

Delivery by inhalation is described further herein. Alternative delivery means include but are not limited to administration intravenously, orally, by inhalation, by cannulation, intracavitally, intramuscularly, transdermally, and subcutaneously.

Therapeutic compositions of the present invention contain a physiologically tolerable carrier together with an airway therapeutic described herein, dissolved or dispersed therein as an active ingredient. In a preferred embodiment, the therapeutic composition is not immunogenic when administered to a mammal or human patient for therapeutic purposes.

The preparation of a pharmacological, composition that contains active ingredients dissolved or dispersed therein is well understood in the art and need not be limited based on formulation. Typically such compositions are prepared as injectables either as liquid solutions or suspensions, however, solid forms suitable for solution, or suspensions, in liquid prior to use can also be prepared. The preparation can also be emulsified.

The active ingredients can be mixed with excipients that are pharmaceutically acceptable and compatible with the active ingredient and in amounts suitable for use in the therapeutic methods described herein. Suitable excipients are, for example, water, saline, dextrose, glycerol, ethanol or the like and combinations thereof. In addition, if desired, the composition can contain minor amounts of auxiliary substances such as wetting or emulsifying agents, pH buffering agents and the like which enhance the effectiveness of the active ingredients.

Exemplary of liquid carriers are sterile aqueous solutions that contain no materials in addition to the active ingredients and water, or contain a buffer such as sodium phosphate at physiological pFH value, physiological saline or both, such as phosphate-buffered saline. Still further, aqueous carriers can contain more than one buffer salt, as well as salts such as sodium and potassium chlorides, dextrose, polyethylene glycol and other solutes D. Controlled Induction of Acute Lung Injury for COPD and IPF Therapy A barrier for treating COPD and IPF is the presence of defective lung tissue in the form of sclerotic terminal bronchioles and alveoli in the case of COPD and scar tissue in pulmonary fibrosis. The simple removal or ablation of this tissue by surgical or ablative technologies (radiofrequency ablation or RFA; photodynamic therapy or PDT; cryoablative therapy or CAT) is often insufficient to trigger stem cell-mediated regeneration. During the regeneration stimulated by influenza-induced ARDS, the distal airway stem cells only migrated to interstitial regions of lung with active immune cell infiltrates. Inducing an inflammatory response in interstitial regions of lung can both dismantle diseased regions of lung in COPD and fibrosis patients as well as trigger the recruitment of stem cells to mediate the regenerative repair.

Methods to induce lung inflammation include the local or systemic application of lipopolysaccharide (LPS), lipid polysaccharide conjugates derived from the outer membranes of Gram-negative bacteria (Ulich et al., 1991; Raetz and Whitfield. 2002). These molecules are known to elicit strong inflammatory responses in mammals via a Toll-like receptor 4-(TLR4) dependent process (Jeyaseelan et al., 2005). LPS is thought to be an important mediator of sepsis-induced ARDS in humans, and peritoneal injections of LPS can induce an ARDS-like phenomenon in mice marked by a generalized interstitial lung inflammation (Gunther et at, 2001). Interestingly, mice who survive LPS injections recover normal lung function and histology without fibrosis, further reinforcing the notion that LPS is yielding an ARDS-like recovery rather than a bleomycin response marked by fibrotic lesions. Thus, LPS represents one means of inducing an ARDS-like phenomenon that potentially promotes a regeneration response involving stem cell such as TASCs or DASCs. Additional triggers of ARDS-like inflammation in the lung include the epidermal growth factor receptor (EGFR) inhibitor Gefitinib (Astrazeneca), which induces acute interstitial lung disease in approximately 1% of patients (Camus et al., 2004; Tammaro et al., 2006; Takada et al., 2011). Significantly, the acute lung damage associated with LPS in mice is greatly augmented by pretreatment with Gefitinib, with results in extended and enhanced inflammation (Suzuki et al., 2003; Inoue et al., 2008). Another trigger could be TNF-α.

In certain embodiments, RFA, PDT, and cryoablation are used in conjunction with instilling inflammatory signals such as those triggered by LPS, TNF-α (Mukhopadhyay et al., 2006) and other inflammatory triggers to mimic those attending infectious ALI known to promote the recruitment of the regenerative response.

IV. Exemplification

The invention now being generally described, it will be more readily understood by reference to the following examples, which are included merely for purposes of illustration of certain aspects and embodiments of the present invention, and are not intended to limit the invention.

Example 1

H1N1 Influenza Infection of Mouse Airways

Mice were infected with a murine-adapted H1N1 (PR8) influenza A by intratracheal aspiration at viral titers of 125 to 1×105 PFU to determine an LD50 of approximately 500 PFU. 250 PFU was chosen as a dose to induce significant damage without lethality. Lungs were harvested at multiple dpi and analyzed by histology and viral protein expression. Viral load was estimated by monitoring the expression of the M2 viral ion channel protein by immunofluorescence, which revealed maximal staining at 4 dpi and a loss of M2 signal by 11 dpi. However, tissue damage, as measured by the degree of immune cell infiltration, appeared to peak at 11 dpi, was reduced at 21 dpi, and was largely cleared across the lung by 60 dpi. These results are mirrored by weight loss in these animals that reaches an extreme at 10-12 dpi and recovers by day 20. At the cellular level, widespread destruction of all airway epithelial cells was observed at 7 dpi resulting in a significant loss of markers for Clara cells (CC10) and ciliated cells (acetylated α-tubulin, TAp73) in the bronchiolar epithelia and AT2 cells (SPC+) of the alveolar epithelium. Damage to airway epithelium is consistent with observations of viral M2 expression in these cells at four days post-infection. The peak of dense infiltrates of immune cells (CD45+) corresponds to the dense histological appearance of the lung at 11-14 dpi.

The H1N1 influenza-infected mice show widespread cytopathic effects and extreme weight loss, and yet both these effects are mitigated between 21-60 dpi. Remarkably, these mice recover without the acquisition of lung fibrosis that accompanies the induction of lung damage by bleomycin, suggesting the possibility that epithelial regeneration underlies recovery from influenza.

Example 2

Emergence of p63-Expressing Cells During Influenza Infection

Figure 2:
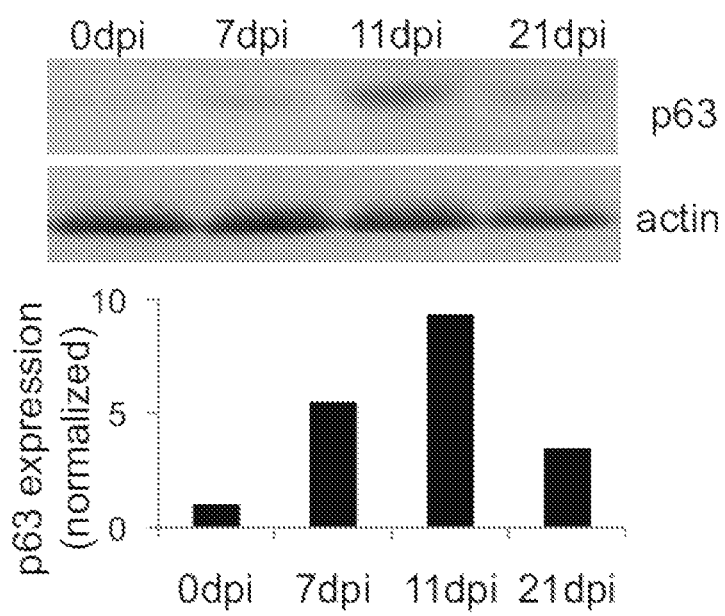
FIG. 2 shows the level of overall p63 protein expression in distal airways.
Figure 3:
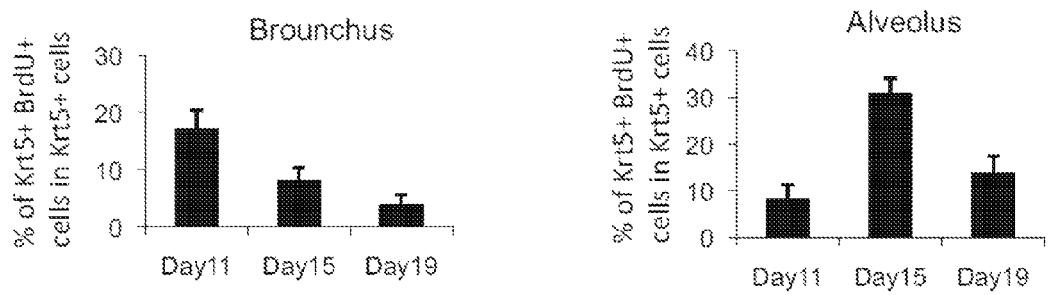
FIG. 3 shows quantification of BrdU+/Krt5+ cells in the interbronchiolar regions.

Given the identification of p63-expressing basal cells as stem cells for nasal and tracheal epithelia of the upper airways (Rock et al., 2009), whether p63-expressing cells might also participate in lung regeneration following influenza infection was explored. Little evidence was found of p63-expressing basal cells in the bronchioles of normal mice. However, by 7 dpi, cells expressing p63 were evident in bronchioles (FIG. 1). By 11 dpi, both p63 cells and Clara cells were found intermingled in the bronchiolar epithelium, and by 21 days most of the bronchiolar epithelium appeared restored at the level of Clara cells while those with p63-expression in the bronchioles were less evident. This rise and fall of p63 expressing cells is reflected in overall p63 protein expression in distal airways (FIG. 2). Unexpectedly, p63-expressing cells were also found in large numbers in the highly damaged lung parenchyma at 11 dpi. On closer inspection, these p63-expressing cells in the damage lung appeared to be clustered in small groups. Using other markers of basal cells, such as antibodies to keratin 5 (Krt5), it was evident that the p63-expressing cells formed discrete clusters or pods (hereafter "Krt5 pods") in interstitial lung. On a gross level, Krt5 pods were distributed in a concentric pattern about bronchioles. BrdU labeling of proliferating cells at 11 dpi revealed robust cell division of the Krt5+ cells in the bronchioles as well as in the Krt5 pods. Direct quantification of BrdU+/Krt5+ cells revealed a progressive decrease in intrabronchiolar regions from 11 dpi and an increase in interbronchiolar regions from 11 dpi (FIG. 3). The appearance of Krt5+ pods in the peribronchiolar regions of lung parenchyma coincides with the pinnacle of influenza-induced lung damage. Krt5+ pods were not observed in the bleomycin-dependent lung fibrosis model.

Example 3

Molecular Analysis of Human Clonogenic Airway Cells

Figure 4:
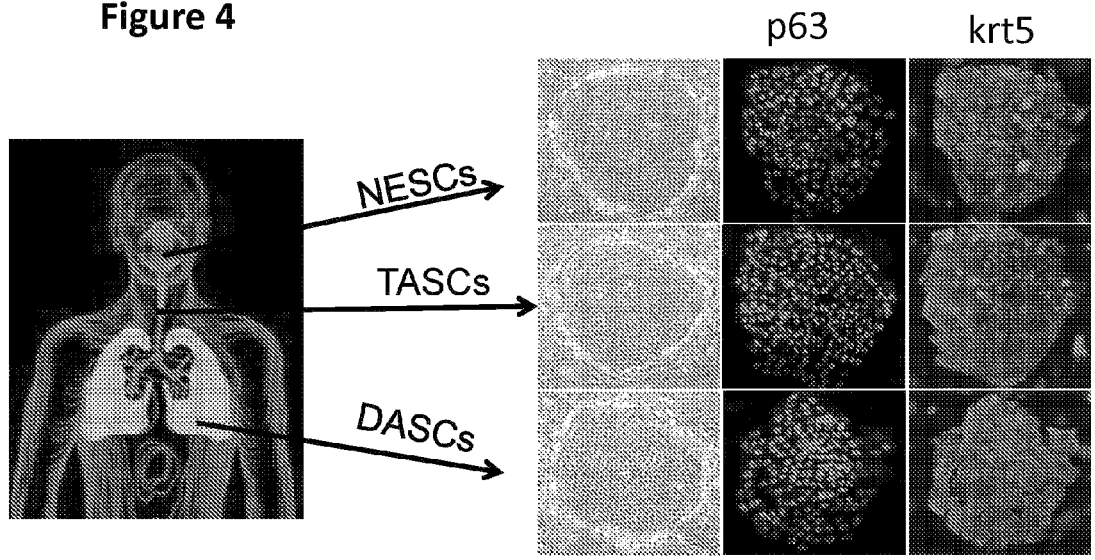
FIG. 4 is a schematic of human airways as source of cells for stem cell cloning. NESCs, nasal epithelial cells; TASCs, tracheobronchial epithelial cells; DASCs, small airway epithelial cells. Left panel, Epithelial cell clones on irradiated Swiss 3T3 cells. Middle panel, p63 immunofluorescence. Right panel, Keratin 5 (Krt5) immunofluorescence.
Figure 5:
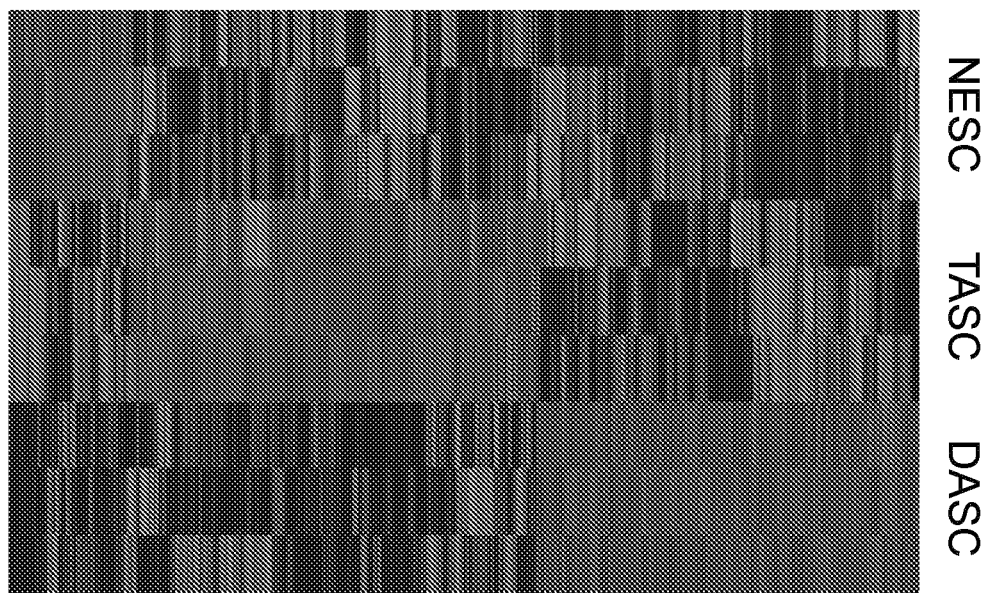
FIG. 5 is a comparative heatmap of NESC, TASC and DASC expression profiles.
Figure 6:
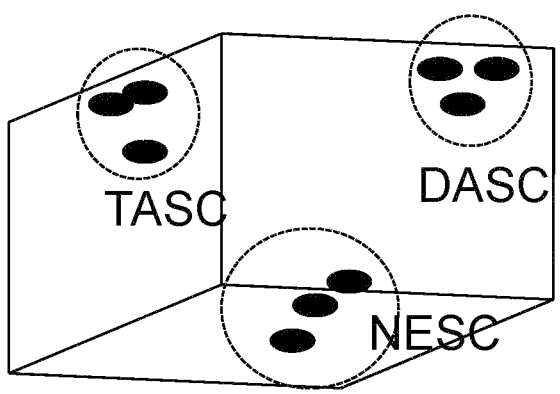
FIG. 6 is a principle component analysis (PCA) of expression microarrays.

To identify distal airway stem cells and assess their relationship to stem cells of the upper airways, single cell cloning methods were employed on populations of human epithelial cells derived from nasal turbinate, tracheobronchial epithelia, and distal airway tissue including bronchioles and alveoli (Rheinwald and Green, 1975; Barrandon and Green, 1987; Senoo et al., 2007). Immature colonies were obtained from approximately 1:500 to 1:2000 cells, and all of these stained uniformly for p63 and for keratin 5 (Krt5) (FIG. 4). These immature clones were provisionally designated nasal epithelial stem cells (NESCs), tracheal airway stem cells (TASCs), and distal airway stem cells (DASCs). About 80 percent of these clones could be propagated further for fat least an additional estimated 50 doublings while maintaining an immature phenotype (not shown). Despite the fact that the original starting cell populations were obtained from disparate regions of the airways, the immature stem cell clones appeared indistinguishable by morphology and staining with basal cell markers. Gene expression datasets from these clones are binned in regiospecific group by unsupervised clustering and by PCA of the whole genome expression patterns despite sharing gene expression of approximately 99 percent of the 17,500 hybridizing genes (FIGS. 5 and 6).

Example 4

Pedigree Tracking of Airway Stem Cells

Figure 7:
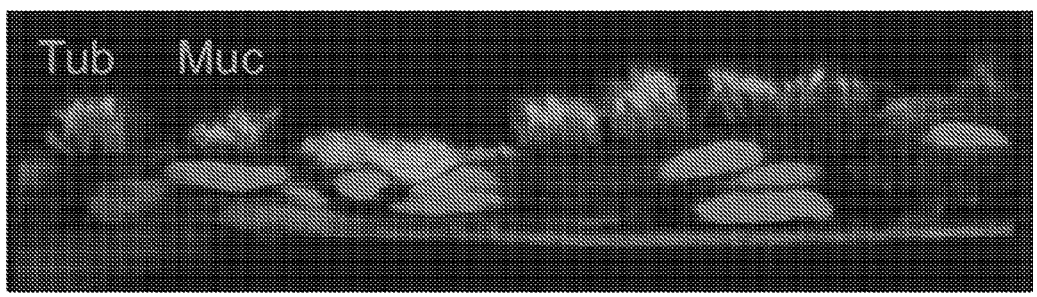
FIG. 7 shows air-liquid interface (ALI) differentiation of NESCs indicated by antibodies to tubulin and mucin 5A to mark ciliated cells and goblet cells, respectively.

The long-term self-renewal potential of the putative human stem cell clones allowed us to isolate independent pedigrees for the analysis of the progeny of a single cell. Expansion of these lines yielded abundant immature cells of known pedigree for a range of differentiation assays to assess lineage potential. For instance, pedigree lines of NESCs were analyzed and posted through multiple differentiation assays. The air-liquid interface model (ALI; Schmidt et al., 1996) has been a powerful tool in airway epithelial differentiation and supports the differentiation of goblet cell and ciliated cells from immature populations of nasal epithelial cells (Usui et al., 2000). Significantly, all pedigree-defined lines of NESCs showed similar distributions of goblet cells and ciliated cells in ALI cultures (FIG. 7), supporting the concept the pedigree lines that were developed from single cells in fact have lineage potential ascribed to NESCs. Whole genome expression analysis of immature, pedigree defined lines and ALI-differentiated cells support this notion and showed an increased expression of genes involved in ciliogenesis (e.g. DYNLRB2, 22.7×; TUBA4b, 9.8×; and DNAH6, 7.2×; all p<0.05) and in goblet cell function (e.g. MUC1, 3.8×; MUC13, 5.6×; and MUC20, 4.51×; all p<0.05). Self-assembling sphere (SAS; Jorissen et al., 1989) cultures of NESCs were also performed. SAS cultures, like the ALI cultures, induce both goblet cell and ciliated cell differentiation from NESCs, and involve the self-assembly of epithelial cells in conditions where cells cannot adhere to a solid support. NESC pedigrees readily assemble into spheres under such conditions within 24 hours, and efficiently undergo both goblet cell and ciliated cell differentiation over the following 15 days upon transfer to differentiation media. Unlike the ALI cultures, which stratify into basal cells and suprabasal differentiated cells, the SAS cultures show a monolayer of ciliated cells and goblet cells polarized to the exterior and lack basal cells altogether. Again, whole genome expression analysis supports the concept that SAS cultures promote ciliogenesis (e.g. increased expression of DYNLRB2, 68.4×; DNAH7, 28.6×; TEKT1, 25.1×; all p<0.05) and goblet cell formation (increased expression of MUC15, 6.7×; MUC20, 7.6×; SCGB2A1, 6.1×; all p<0.05) from NESCs. In contrast to their similar differentiation programs in ALI and SAS cultures, NESCs behaved very differently in 3-D Matrigel cultures. NESCs showed robust formation of solid spheres in Matrigel between days 5 and 10, which subsequently hollow with the addition of differentiation media, and by day 21 show immature cells at the periphery and cells with squamous differentiation towards the lumen. This squamous metaplasia is supported by the comparison between gene expression of undifferentiated NESCs and those differentiated for 21 days in Matrigel, which show strong expression of squamous epithelial genes (e.g. LCE2B, 173.1×; KRT10, 6.0×; and SPRR2A, 4.5×; all p<0.05). Similar development of a squamous metaplasia has been seen with the differentiation of nasal turbinate epithelial cell populations (Endres et al., 2005), suggesting that pedigree-defined cells retain the capacity for this pathway of differentiation. Overall gene expression PCA indicates that each of these differentiation assays yields different outcomes marked by a stratified airway epithelium in ALI cultures, a non-stratified airway epithelium in SAS cultures, and a squamous metaplasia in 3-D Matrigel cultures.

Example 5

DASC Pedigrees Assemble into Alveolar-Like Structures In Vitro

Defined pedigrees of TASCs and DASCs were grown in ALI cultures to compare their differentiation potential with that of NESC lines. Like the NESC lines, the TASC pedigrees showed robust differentiation into ciliated cells and mucin-producing goblet cells during the 21-day period of ALI culture. In contrast, the DASC pedigrees showed only minor indications of mucin expression, rare ciliated cell formation, and occasional CC10 expression indicative of Clara cells. The TASC lines further differed from the DASC lines in their degree of stratification in ALI cultures. The TASCs presented a multilayered epithelium with p63-positive basal cells underneath differentiated goblet and ciliated cells, while the DASC pedigrees retain a monolayer appearance over the differentiation period. Gene expression analysis of the ALI cultures of TASC and DASC lineages confirmed these observations, with the differentiated TASC cultures showing high expression of genes involved in ciliogenesis, mucin production, and epithelial stratification compared to DASCs grown in ALI culture. In 3-D Matrigel cultures, the TBEC lines, like the NESC pedigrees, underwent squamous metaplasia. Curiously, the DASC pedigree lines also assemble into spheres but ultimately these hollow and collapse into multispherical structures by day 21. The hollowing effect appears to be the direct consequence of apoptosis as these cells within the spheres show robust activated caspase-3 staining. The multispherical entities formed from DASC lines do not stratify but appear to be comprised of unilaminar cellular assemblies that express the alveolar type I marker PDPN. These same structures are labeled with the 4C10 monoclonal antibody that recognizes a ca. 300 kDa protein specific to human alveoli.

Consistent with the divergent differentiation of the TASC and DASC pedigrees in Matrigel cultures, datasets of whole genome microarrays of the structures assembled in 3-D cultures by these lines showed large differences including a host of genes implicated in alveolar structure or formation, including MGP, SPAC, ANGPT1, LIMCH1, CHI3.3L1, KDR, PECAM, ANXA3, SLC39A8, ERRF11, PDPN and TSPAN8. These findings were supported by wider Gene Set Enrichment Analysis (GSEA), which showed the squamous metaplasia of the TASC Matrigel structures expressed genes associated with epidermal development. In contrast, the DASC-derived structures showed high expression of genes associated with angiogenesis regulation, monocation transport (Matthay et al., 2002; Eaton et al., 2009), an important physiological function of AT cells, and synaptic transmission, a possible reflection of the importance of neurogenic control of alveolar function (Sakuma et al., 2006).

Example 6

Assembly of Alveoli-Like Structures Conserved in Rodent-Derived DASC Pedigrees

Figure 8:
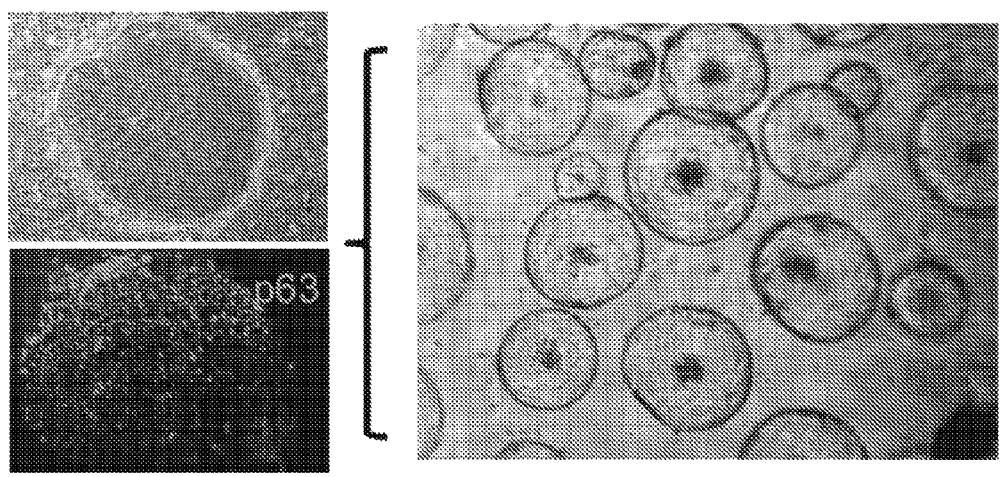
FIG. 8 shows rat DASCs on 3T3 cells derived from single cell suspension of deep lung tissue. Top left: Phase contrast; Bottom left: Immunofluorescence with anti-p63 antibodies. Middle panel: Image of unilaminar structures produced by rat DASC pedigree-specific lines after 21 days in 3-D Matrigel culture. The scale bar represents 50 mm.
Figure 9:
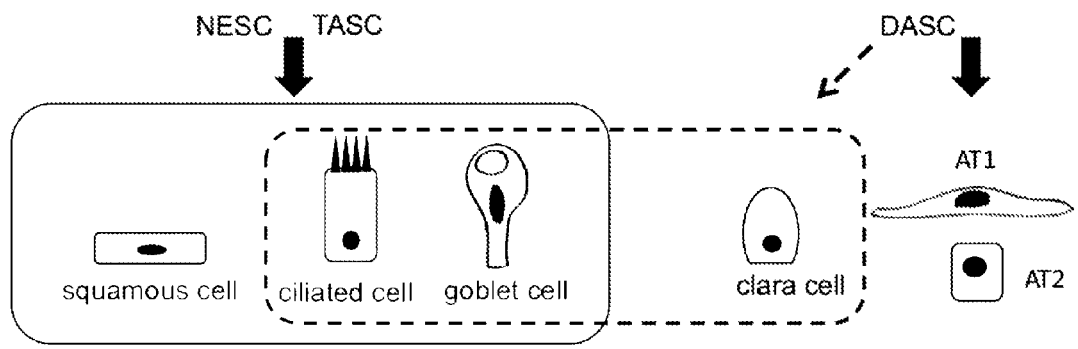
FIG. 9 is a schematic of the differentiation potential of regiospecific airway stem cells derived from multiple in vitro models.
Figure 10:
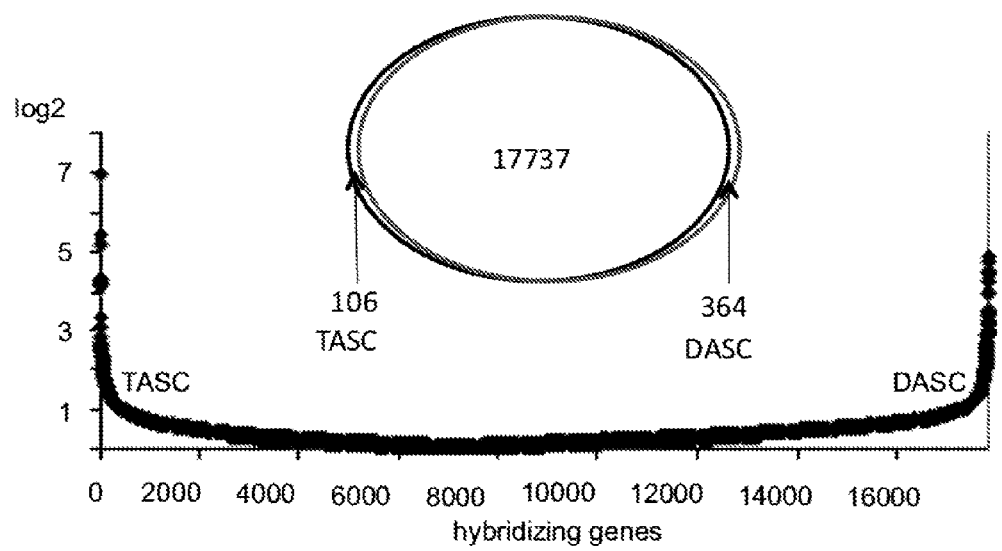
FIG. 10 is a Venn diagram depicting differentially expressed genes between TASC and DASC stem cell pedigrees, while the graphics below indicate the absolute foldchange in gene expression between TASC and DASC among more than 17,000 informative genes.

To test whether similar p63-expressing stem cells could be derived from the deep lung of non-human species, multiple immature clones were obtained from distal airways of six-week-old rats. Defined pedigrees were developed from several of these that were subsequently grown in 3-D Matrigel cultures. All of the rat pedigree-specific DASC lines formed uniform solid spheres after 10 days of growth that subsequently hollowed over the next 11 days (FIG. 8). To determine whether these structures contain proteins linked to alveoli in vivo, a panel of monoclonal antibodies were generated from mice immunized to rat distal airway tissue. Monoclonal antibodies 13A1 and 54D1 are specific to rat alveoli and recognize proteins with molecular masses of 45 and 25 kDa, respectively. These antibodies, which do not stain rat immature rat DASC clones, efficiently stain the unilaminar structures produced by the DASC pedigree lines. These data suggest that these alveolar-like structures express genes found in alveoli. Further, the DASCs described herein are fully committed to alveolar lineages with additional potential to form Clara, ciliated, and mucin producing cells and therefore distinct from the TASCs and NESCs that are committed to ciliated cells, goblet cells, and as well can undergo squamous metaplasia (FIG. 9). Despite these differences in lineage commitment, DASCs show only minor differences in gene expression compared with TASCs and NESCs in the range of 100-200 genes (FIGS. 10 and 11).

Example 7

Influenza-Infected Lung Displays a Massive Increase in Clonogenic Basal Cells

To probe the basal-like cells observed in infected lung, dissociated distal airway tissues were plated in clonogenic assays. The colonies that arose were uniform in appearance from the infected and control lungs and were composed of small, p63-expressing immature cells and expressed Krt5. When grown on Matrigel cultures, cells from these colonies form solid spheres that hollow through cell death to yield unilaminar structures similar to those generated by human DASCs. These unilaminar structures stain for antibodies to aquaporin 5 (Aqp5), a marker of alveoli. A comparison of expression performed on RNA amplified from individual clones and the Matrigel structures formed from them showed reproducible differences in gene expression. The immaturity markers Krt5 and Krt14 are lost in during differentiation in Matrigel, while markers of alveoli, such as Aqp5 and surfactant proteins Sfipal, Sflpb, and Sftpc, are all upregulated in these structures. Consistent with the appearance of large numbers of p63-positive cells in lung parenchyma following H1N1 influenza infection, a several hundred-fold increase in p63-expressing clonogenic cells in infected lungs was observed.

Whole genome microarray revealed reproducible differences in 358 genes among three clones from control and infected lungs. One of the genes proved to be keratin 6A (Krt6a), a known marker of migrating keratinocytes during wound healing in the epidermis (Wojcik et al., 2000). Expression of this gene alone differentiates between the clones derived from control lung and 12 dpi lung. In vivo, Krt6 antibodies differentiate between basallike cells in Krt5 pods of interstitial regions from basal cells of bronchioles whereas Krt5 antibodies recognize both these ectopic basal cells and those in the bronchiolar epithelium. GSEA of the expression data sets derived from the distal airway colonies revealed a bias for genes involved in wound healing, tissue development, and regulation of growth in those from infected mice.

Example 8

Krt5 Pods Linked to Lung Regeneration

The ability of human distal airway stem cells to form alveoli-like structures in vitro suggested that the Krt5 pods of basal-like cells seen in the influenza-damaged lung were components of a regenerative process. Consistent with this, the general appearance of individual Krt5 pods at 11 dpi was one of tight clusters of cells, while at 15 and 21 dpi many of these pods had lumens reminiscent of alveoli. Direct quantification of these Krt5 pod "types" over time confirmed this notion, suggesting a progression over 10 days from a tight group of Krt5+ cells to structures resembling alveoli. Whether the Krt5 pods would stain with a new monoclonal antibody generated from mice immunized with human fetal lung designated here as "11B6" was explored. 11B6 reacts specifically to alveolar regions of mouse lung but not to bronchioles. Staining of regions of damaged lung containing Krt5 pods with the 11B6 monoclonal antibody revealed co-localization of the two antigens especially in those pods with larger diameters, suggesting a specificity for those Krt5 pods with larger lumens. Quantification of this link between 11B6 and Krt5+ pods also correlated with dpi. The Krt5 pods were also probed with antibodies to PDPN, which shows an alveoli-specific pattern in normal lung. PDPN antibodies also co-localize with Krt5 pods.

In assessing the influenza-infected lung from a panoramic view, three distinct areas were observed: normal appearing lung parenchyma with histologically normal alveoli, damaged regions marked by semi-dense infiltrate and Krt5 pods, and damaged regions marked by highly dense infiltrates but without Krt5 pods. Krt5+ pods were not observed in regions of histologically normal lung tissue. The presence of Krt5 pods in less-densely infiltrated regions is that these regions are undergoing regenerative repair and clearing dense immune cell infiltrates in the process. Indeed the regions marked by Krt5+ pods show intermingled, CD45-positive immune cells in the immediate proximity. Also, within regions of dense infiltrate were bronchioles that lacked Krt5-positive basal cells, whereas bronchioles associated with satellite Krt5-positive pods also had Krt5-positive basal cells. This observation reflects the possibility that if the infection eradicates the bronchiolar epithelium, it may be incapable of spawning a peribronchiolar population of Krt5 pods.

Example 9

Krt5 Pods at Sites of Lung Regeneration

Figure 12:
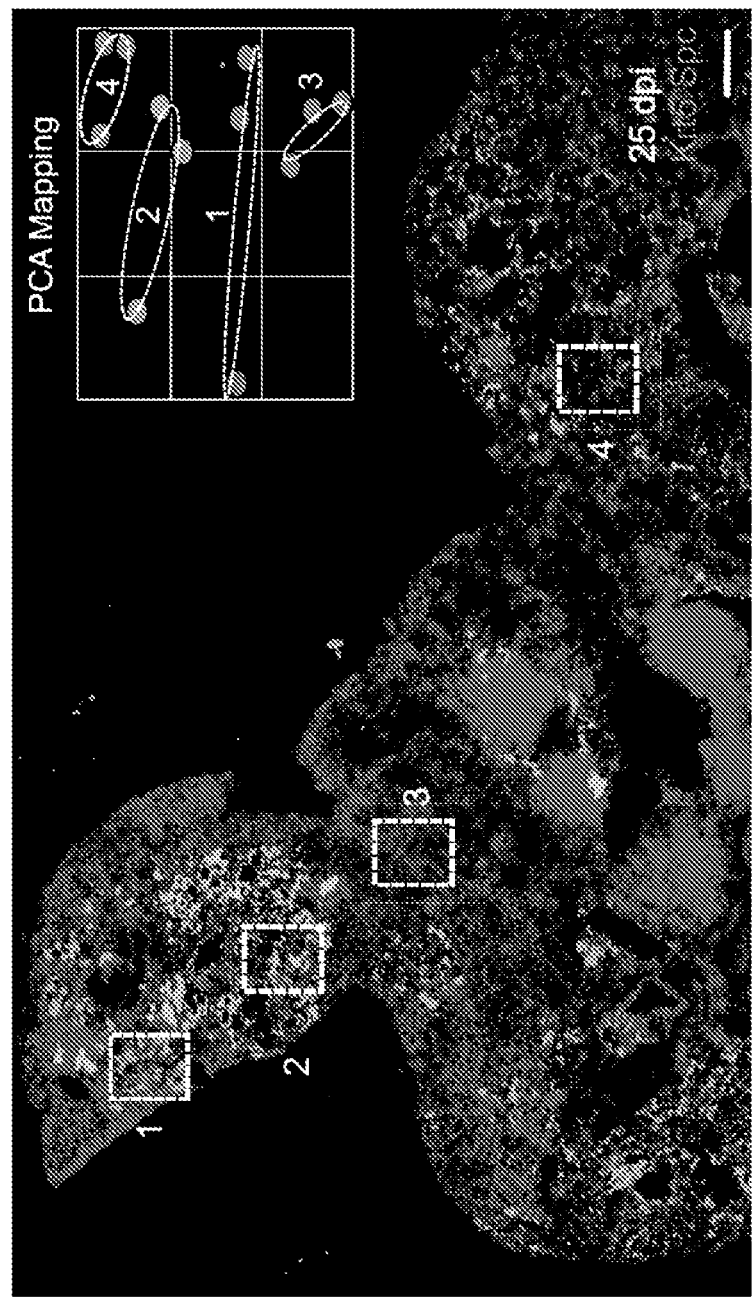
FIG. 12 shows a section of 25 dpi lung stained with antibodies to Krt5, SPC, and counterstained with DAPI. Four regions are demarcated with boxes as laser capture microdissection targets (1) SPC+ cells in densely infiltrated zones, (2) Krt5 pods, (3) SPC-/Krt5- zones with dense infiltrates, and (4) SPC+ cells in normal lung. Inset shows PCA of three independent LCM samples corresponding to regions 1-4. The scale bar represents 200 mm.
Figure 13:
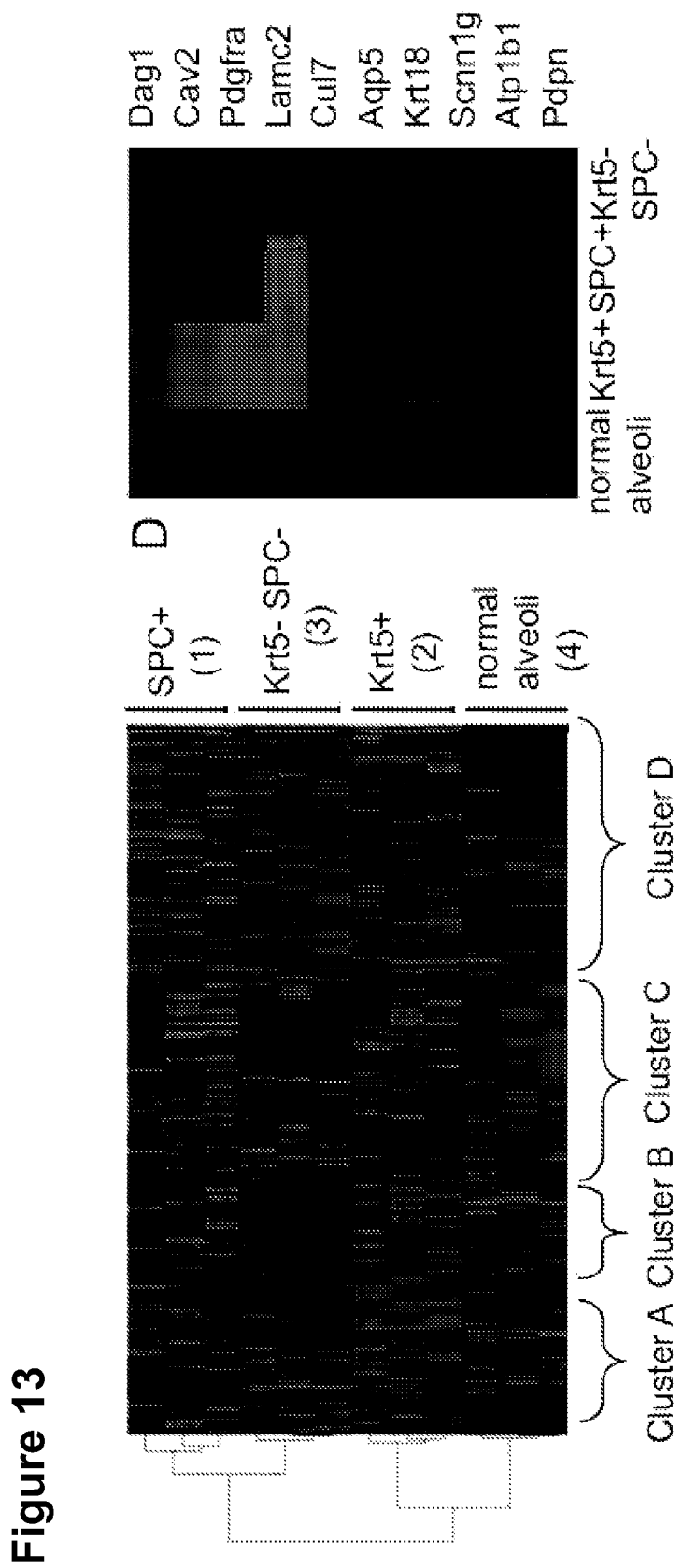
FIG. 13 shows a heatmap of 2205 differentially expressed genes with p value<0.05 derived from LCM samples of regions 1-4. Gene clusters A-D are indicated. The left panel is a heatmap indicating relative expression of individual genes linked to alveoli in the datasets corresponding to regions 1-4.
Figure 14:
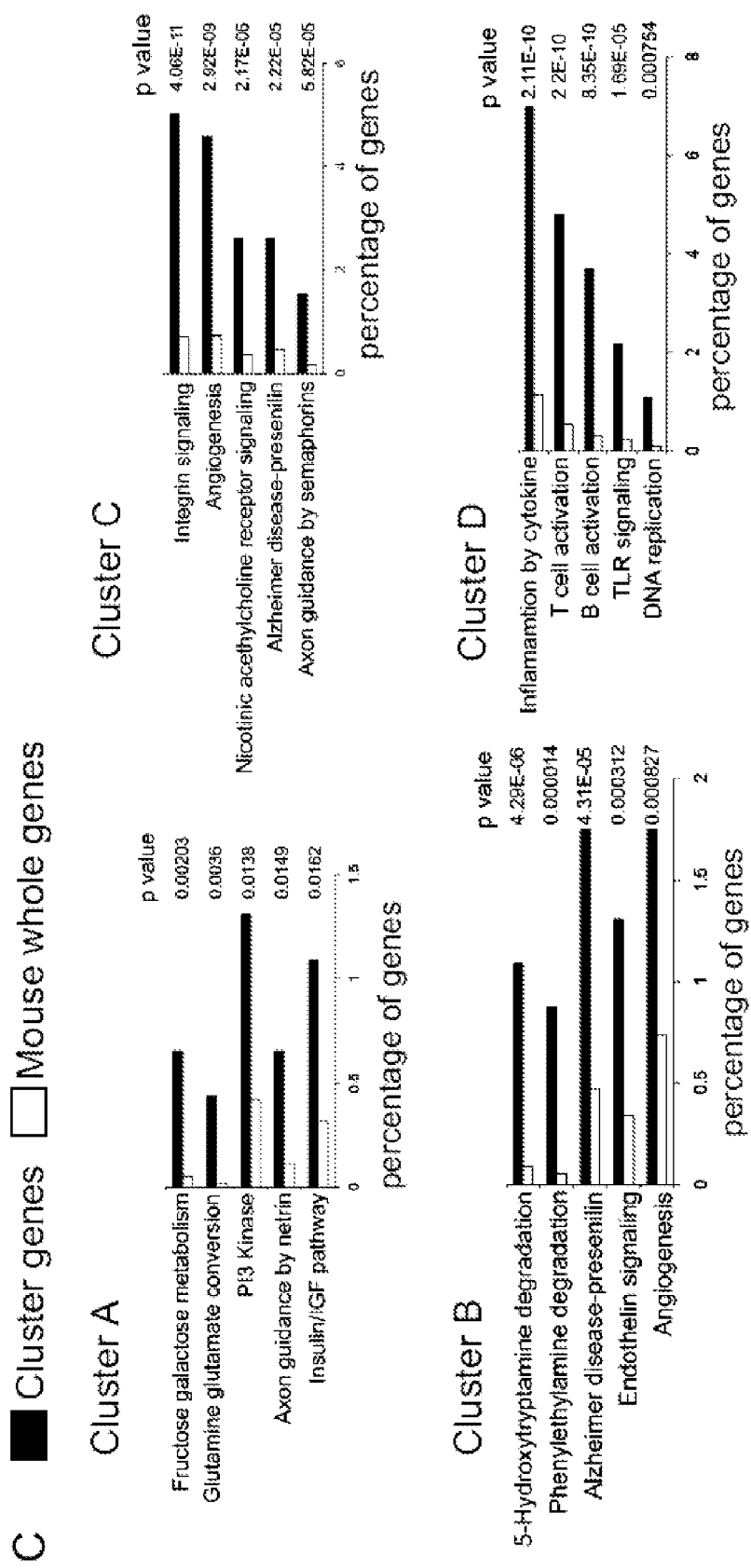
FIG. 14 shows a gene ontology analysis of gene clusters A-D indicated in heatmap together with associated p values.

Laser capture microdissection (LCM) was used to isolate RNA for expression microarray analysis from frozen sections of 25 dpi lung regions rich in Krt5 pods, normal or repaired lung, or regions of high-density infiltrates without obvious repair. The regions of high-density infiltrates without obvious alveoli were further divided into regions with and without SPC, a marker of alveolar type II cells (FIG. 12). PCA of these datasets revealed that the regions rich in Krt5 pods were most closely related to the regions of normal or repaired lung (FIG. 12, inset). This impression is reinforced by a heatmap of differentially expressed genes in these datasets which shows the similarity between the densely infiltrated regions devoid of alveolar markers and the densely infiltrated, SPC+ regions marked as Cluster D genes (FIG. 13). Cluster D genes included strong representations by immune cell functions and innate immune signaling consistent with the persistence of a dense infiltration of immune cells (FIGS. 14 and 15). In contrast, the regions with Krt5 pods showed significant overlap with normal lung in a gene set designated Cluster B including genes involved with angiogenesis and endothelin signaling (Khimji and Rockey, 2010), as well as aromatic amine degradation known to be functionally linked to lung endothelial cells (Gillis and Pitt, 1982) (see FIGS. 14 and 15). Additionally, Cluster B showed an overrepresentation by genes involved in Wnt, Hedgehog, and nicotinic acetylcholine receptor signaling. Together, these data suggested that the Krt5 pods are in association with elements of endothelial cells involved in capillary formation. Moreover, Cluster B genes include an array of alveolar genes not expressed in regions of damaged lung lacking Krt5 pods (marked by the SPC+/Krt5− or SPC−/Krt5−) (see FIGS. 14 and 15), including PDPN, caveolin 2, Aqp5, and PDGFRα. Cluster C genes, those overrepresented only in regions non-damaged lung, are characterized by gene sets associated with integrin signaling, angiogenesis, nicotinic acetylcholine receptor signaling, and axon guidance by semaphorins (see FIGS. 14 and 15). Consistent with the link between Krt5 pods and lung regeneration, robust co-localization of Krt5 and the alveolar-specific monoclonal antibody 11B6 was seen, but no 11B6 staining of damaged regions regardless of whether they have SPC staining. On the broadest level, these data support the notion that regions with Krt5 pods express genes similar to apparently normal or repaired lung, and very different from regions marked by severe damage. They also suggest a dynamic process involving a host of pathways whose significance for the recovery from ARDS will require extensive empirical validation.

Example 10

Lineage Tracing of Alveolar Progenitors from Bronchioles to Alveoli

While clusters of Krt5+ pods always appear in a peribronchiolar pattern in influenza infected lung about bronchioles with Krt5+ cells, their origins remained to be established. To test whether the Krt5 cells that appear in the bronchioles are indeed the origins of the parenchymal Krt5+ pods, standard lineage tracing methods based on Tamoxifen dependent LacZ expression driven by Cre recombinase from the keratin 14 (Krt14) promoter (Mao et al., 1999; Vasioukhin et al., 1999) were used. Krt14-positive cells are not present in bronchioles prior to infection but become evident at 4 days post-infection as the same cells expressing Krt5 and increase in numbers through day 9 while remaining restricted to the bronchioles. At or around 11 dpi, there appears to be a concerted migration of these Ktr5/Krt14 positive cells to interstitial lung and the appearance of Krt5 pods. Treatment of these mice with daily injections of Tamoxifen at 5, 6, and 7 dpi resulted in labeling of both the bronchioles and the Krt5+ pods at 25 dpi. These data are consistent with the notion that the Krt5+ pods arise from cells that migrate from the bronchioles to local sites of interbronchiolar lung damage.

Example 11

Experimental Procedures

Animal Models
C57/Bl6 adult mice were infected with a sublethal dose of Influenza H1N1 A/PR8/34 mouse adapted virus by intratracheal inhalation and lungs were harvested at various time points post infection. For BrdU incorporation assays 30 mg/kg BrdU in sterile PBS was administered IP and mice were sacrificed at different time points post injection. All procedures were conducted under IACUC guidelines and approved protocols. For bleomycin experiments, mice were treated with 6 U/kg bleomycin by intratracheal instillation and were sacrificed at different time points post treatment to harvest lungs.

Histology and Immunofluorescence
Mice were sacrificed and lungs were inflated and fixed with 4% formaldehyde prior to paraffin embedding. Antibodies included influenza virus A M2 protein (Abcam), p63 (4A4 clone), alveolar markers (13A1, 54D1, 4C10, 11B6 clone), Krt5 (Neomarkers, Lifespan Biosciences), MucSAc, CC10, SPC, Pdpn, Aqp5, Cd45 (Santa Cruz), BrdU (Accurate Chemical), p73 (3A6 clone), Ivl, Krt14, Krt10, Krt6 (Covance), pan-Keratin, SMA and acetylated alpha tubulin (Sigma). Appropriate Alexa flour 488 or 594 conjugated secondary antibodies (Invitrogen) were used for IF and Vector Labs ABC kit with DAB substrate (Vector laboratories) were used for IHC. Murine monoclonal antibodies were generated to human 22 wk fetal lung tissue under IRB approval using standard methods (Kohler and Milstein, 1975).

Microarray and Bioinformatics
RNAs obtained from LCM and colonies were amplified using the WT Pico RNA Amplification System, WT-Ovation Exon Module and Encore Biotin Module (NuGEN Technologies) and hybridized onto GeneChip® Mouse Exon 1.0 ST Array.

GeneChip operating software was used to process all the Cel files and calculate probe intensity values. To validate sample quality probe hybridization ratios were calculated using Affymetrix Expression Console software. The intensity values were log 2-transformed and imported into the Partek Genomics Suite 6.5(beta). Exons were summarized to genes and a 1-way ANOVA was performed to identify differentially expressed genes. P values and fold-change were calculated for each analysis. Heatmaps were generated using Pearson's correlation and Ward's method and Principal Component Analysis was conducted using all probe sets. Pathway analyses were performed using Gene Set Enrichment Analysis (GSEA) software and PANTHER database (Subramanian et al., 2005; Yuan et al., 2009).

Example 12

Models for Acute Lung Injury

1. Acute Lung Injury
A combination of LPS and EGFR inhibitors is used to induce acute lung injury (ALI) in mice. The LD50 of LPS and EGFR inhibitors are determined. Also, histology and immunohistochemistry for p63. Krt5, and lung marker monoclonal antibodies is tracked in survivors at day 7, day 1, and day 21.

EGFR inhibitor (Gifitinib) is dosed on day 1, 2, and 3 with day 3 including 1-300 µg of LPS. The reported LD50 for LPS is 150-300 µg and that the EGFR inhibitor should synergize with the LPS in the induction of ALI. Survivors will be sacrificed at day 7, 11, and 21 and lungs examined by histology and IHC with various markers to assess the degree of ALI and the extent of lung repair and ultimately how much this process compares with lung regeneration following influenza infection.

2. ALI in Chronic Lung Fibrosis

Fibrosis is induced with intratracheal or intraperitoneal bleomycin. ALI is then induced with sub-LD50 EGFRi+ LPS.

3. Administration of Stem Cells

Exogeneous stem cells are administered to determine if they incorporate into regenerating lung following ALI with or without fibrosis. Distal airway stem cells are cloned and expanded in colonies from GFP-expressing mice, and are added via tracheal cannulation.

Example 13

Method of Isolating Stem Cells

Human nasal, trachea or lung tissue specimens were washed with cold washing medium (DMEM: F12 1:1 (Gibco), 100 µg/ml pen strep, 1001 g/ml gentamicin)). The samples were then cut into small pieces and digested with digestion medium (DMEM: F12 1:1, 100 µg/ml pen strep, 1004 µg/ml gentamicin, 5% fetal bovine serum. 2 mg/ml collagenase) at 37° C. for 1 hour. The mixture of cells were spun down and washed by washing buffer three times. The cells were then resuspended in growth medium (5 mg/ml insulin, 10 ng/ml EGF, $2 \times 10^{-9}$ M 3,3',5-triiodo-L-thyronine, 0.4 mg/ml hydrocortisone, 24 mg/ml adenine, $1 \times 10^{-10}$ M cholera toxin in DMEM/Ham's F12 3:1 medium with 10% fetal bovine serum), filtered through a 70 µm nylon cell strainer (BD Falcon) and plated on lethally irradiated 3T3-J2 fibroblast feeders.

REFERENCES

Barrandon Y, and Green H. (1987). Three clonal types of keratinocyte with different capacities for multiplication. Proc Natl Acad Sci USA 84, 2302-2306.

Belser J A, Szretter K J, Katz J M, and Tumpey T M. (2009). Use of animal models to understand the pandemic potential of highly pathogenic avian influenza viruses. Adv. Virus Res. 73, 55-97.

Berthiaume Y, Lesur O, and Dagenais A. (1999). Treatment of adult respiratory distress syndrome: plea for rescue therapy of the alveolar epithelium. Thorax 54, 150-160.

Cole B B, Smith R W, Jenkins K M, Graham B B, Reynolds P R, and Reynolds S D. (2010) Tracheal basal cells: a facultative progenitor cell pool. Am. J. Pathol. 177, 362-376.

Eaton, D. C., Helms, M. N., Koval, M., Bao, H. F., and Jain, L. (2009). The contribution of epithelial sodium channels to alveolar function in health and disease. Annu Rev Physiol 71, 403-423.

Gao P, Watanabe S, Ito T, Goto H, Wells K, McGregor M, Cooley A J, and Kawaoka Y. (1999). Biological heterogeneity, including systemic replication in mice, of H5N1 influenza A virus isolates from humans in Hong Kong. J. Virol. 73, 3184-3189.

Giangreco A, Reynolds S D, and Stripp B R. (2002). Terminal bronchioles harbor a unique airway stem cell population that localizes to the bronchoalveolar duct junction. Am. J. Pathol. 161, 173 . . . 182.

Giangreco A Arwert E N, Rosewell I R, Snyder J, Watt F M, and Stripp B R. (2009). Stem cells are dispensable for lung homeostasis but restore airways after injury. Proc. Natl. Acad. Sci. USA 106, 9286-9291.

Gill J R, Sheng Z M. Ely S F, Guinee D G, Beasley M B, Sub J, Deshpande C, Mollura D J, Morens D M, Bray M, Travis W D, and Taubenberger J K. (2010). Pulmonary pathologic findings of fatal 2009 pandemic influenza A/H1N1 viral infections. Arch. Pathol. Lab. Med. 134, 235-243.

Gillis, C. N., and Pitt, B. R. (1982). The fate of circulating amines within the pulmonary circulation. Annu. Rev. Physiol. 44, 269-281.

Green, H. (2008). The birth of therapy with cultured cells. Bioessays 30, 897-903.

Gubareva L V, McCullers J A, Bethell R C, and Webster R G. (1998). Characterization of influenza A/HongKong/156/97 (H5N1) virus in a mouse model and protective effect of zanamivir on H5N1 infection in mice. J. Infect. Dis. 178, 1592-1596.

Herridge M S, Cheung A M, Tansey C M, Matte-Martyn A, Diaz-Granados N, Al-Saidi F, Cooper A B, Guest C B, Mazer C D, Mehta S, Stewart T E, Barr A, Cook D, and Slutsky A S; Canadian Critical Care Trials Group. (2003). One-year outcomes in survivors of the acute respiratory distress syndrome. N. Engl. J. Med. 348, 683-693.

Hong K U, Reynolds S D, Watkins S, Fuchs E, and Stripp B R (2004). In vivo differentiation potential of tracheal basal cells: Evidence for multipotent and unipotent subpopulations. Am J Physiol Lung Cell Mol Physiol 286: L643-649.

Hoshino T, Okamoto M, Sakazaki Y, Kato S, Young H A, and Aizawa H. (2009). Role of proinflammatory cytokines IL-18 and IL-1beta in bleomycin-induced lung injury in humans and mice. Am. J. Respir. Cell. Mol. Biol. 41, 661-670.

Kajstura J, Rota M, Hall S R, Hosoda T, D'Amario D, Sanada F, Zheng H, Ogórek B, Rondon-Clavo C, Ferreira-Martins J, Matsuda A, Arranto C, Goichberg P, Giordano G, Haley K J, Bardelli S, Rayatzadeh H, Liu X, Quaini F, Liao R, Leri A, Perrella M A, Loscalzo J, and Anversa P. (2011). Evidence for human lung stem cells. N Engl J Med. 364, 1795-1806.

Khimji, A. K., and Rockey, D. C. (2010). Endothelin—biology and disease. Cell Signal. 22, 1615-1625.

Kim C F, Jackson E L, Woolfenden A E, Lawrence S, Babar I, Vogel S, Crowley D, Bronson R T, and Jacks T. (2005). Identification of bronchioalveolar stem cells in normal lung and lung cancer. Cell 121, 823-835.

Köhler, G., and Milstein C. (1975). Continuous cultures of fused cells secreting antibody of predefined specificity. Nature 256, 495-497.

Lowy R J. (2003). Influenza virus induction of apoptosis by intrinsic and extrinsic mechanisms. Int Rev Immunol. 22, 425-449.

Lu X, Tumpey T M, Morken T, Zaki S R, Cox N J, and Katz J M. (1999). A mouse model for the evaluation of pathogenesis and immunity to influenza A (H5N1) viruses isolated from humans. J. Virol. 73, 5903-5911.

Mao X, Fujiwara Y, and Orkin S H. (1999). Improved reporter strain for monitoring Cre recombinase-mediated DNA excisions in mice. Proc Natl Acad Sci USA. 96, 5037-5042.

Matthay, M. A., Folkesson, H. G., and Clerici, C. (2002). Lung epithelial fluid transport and the resolution of pulmonary edema. Physiol Rev 82, 569-600.

Mendelsohn M G. Dilorenzo T P. Abramson A L, and Steinberg B M. (1991). Retinoic acid regulates, in vitro, the two normal pathways of differentiation of human laryngeal keratinocytes. In Vitro Cell Dev Biol. 27A, 137-141.

Matuschak G M, and Lechner A J. (2010). Acute lung injury and the acute respiratory distress syndrome: pathophysiology and treatment. Mo. Med. 107, 252-258.

Moore, B. B., and Hogaboam, C. M. (2008). Murine models of pulmonary fibrosis. Am. J. Physiol. Lung. Cell. Mol. Physiol. 294, 1.152-160.

Mori I, Komatsu T, Takeuchi K, Nakakuki K, Sudo M, and Kimura Y. (1995). Viremia induced by influenza virus. Microb. Pathog. 19, 237-244.

Nakajima N, Sato Y. Katano H. Hasegawa H, Kumasaka T, Hata S, Tanaka S, Amano T, Kasai T, Chong J M, Iiduka T, Nakazato 1, Hino Y, Hamamatsu A, Horiguchi H, Tanaka T, Hasagawa A. Kanaya Y, Oku R. Oya T, Sata T. (2011). Histopathological and immunohistochemical findings of 20 autopsy cases with 2009 H1N1 virus infection. Mod Pathol. 2011 (ahead of print).

Narasaraju T, Ng H H, Phoon M C, and Chow V T. (2010). MCP-1 antibody treatment enhances damage and impedes repair of the alveolar epithelium in influenza pneumonitis. Am. J. Respir. Cell. Mol. Biol. 42, 732-743.

Ramsey, C., and Kumar, A. (2011). H1N1: viral pneumonia as a cause of acute respiratory distress syndrome. Curr. Opin. Crit. Care 17, 64-71.

Rheinwald J G, and Green H. (1975). Serial cultivation of strains of human epidermal keratinocytes: the formation of keratinizing colonies from single cells. Cell 6, 331-343.

Rawlins, E. L., Okubo. T., Xue, Y., Brass, D. M., Auten, R. L., Hasegawa, H., Wang. F., and Hogan, B. L. (2009). The role of Scgb1a1+Clara cells in the long-term maintenance and repair of lung airway, but not alveolar, epithelium. Cell Stem Cell 4, 525-534.

Rock J R, Onaitis M W, Rawlins E L, Lu Y, Clark C P, Xue Y, Randell S H, and Hogan B L. (2009). Basal cells as stem cells of the mouse trachea and human airway epithelium. Proc. Natl. Acad. Sci. USA. 106, 12771-12775.

Rock J R, Randell S H, and Hogan B L. (2010). Airway basal stem cells: a perspective on their roles in epithelial homeostasis and remodeling. Dis. Model Mech. 3, 545-56.

Sakuma, T., Gu, X., Wang, Z., Maeda, S., Sugita, M., Sagawa, M., Osanai, K., Toga, H., Ware, L. B., Folkesson, G., and Matthey, M. M. (2006). Stimulation of alveolar epithelial fluid clearance in human lungs by exogenous epinephrine. Crit Care Med 34, 676-681.

Schmidt, D., Hubsch, U., Wurzer, H., Heppt, W., and Aufderheide, M. (1996). Development of an in vitro human nasal epithelial (HNE) cell model. Toxicol Lett 88, 75-79.

Senoo M., Pinto F., Crum C. P., and McKeon F. (2007). p63 is essential for the proliferative potential of stem cells of stratified epithelia. Cell 129, 523-536.

Stripp, B. R., and Reynolds. S. D. (2008). Maintenance and repair of the bronchiolar epithelium. Proc. Am. Thorac. Soc. 5, 328-333.

Subramanian A. Tamayo P., Mootha V. K., Mukherjee S., Ebert B. L., Gillette M. A., Paulovich A., Pomeroy S. L., Golub T. R., Lander E. S., and Mesirov J. P. (2005). Gene set enrichment analysis: a knowledge-based approach for interpreting genome-wide expression profiles. Proc. Natl. Acad, Sci. USA 43, 15545-15550.

Usui S, Shimizu T, Kishioka C, Fujita K, Sakakura Y. (2000). Secretory cell differentiation and mucus secretion in cultures of human nasal epithelial cells: use of a monoclonal antibody to study human nasal mucin. Ann Otol Rhinol Laryngol. 109, 271-277.

Vasioukhin, V., Degenstein, L., Wise, B., and Fuchs, E. (1999). The magical touch: genome targeting in epidermal stem cells induced by tamoxifen application to mouse skin. Proc. Natl. Acad. Sci. U.S.A. 96, 8551-8556.

Wu S, Metcalf J P, and Wu W. (2011). Innate immune response to influenza virus. Curr Opin Infect Dis. 24, 235-240.

Wojcik S M, Bundman D S, and Roop D R. (2000). Delayed wound healing in keratin 6a knockout mice. Mol. Cell. Biol. 20, 5248-5255.

Yang, A., Kaghad, M., Wang, Y., Gillette, E., Fleming, M. D., Dotsch. V., Andrews, N. C., Caput, D., and McKeon, F. (1998). p63, a p53 homolog at 3q27-29, encodes multiple products with transactivating, death-inducing, and dominant-negative activities. Mol. Cell 2, 305-316.

Yang, A., Schweitzer, R., Sun, D., Kaghad, M., Walker, N., Bronson, R. T., Tabin. C., Sharpe, A., Caput, D., Crum, C., and McKeon, F. (1999). p63 is essential for regenerative proliferation in limb, craniofacial and epithelial development. Nature 398, 714-718.

Yuan P., Han J., Guo G., Orlov Y. L., Huss M., Y Loh Y H., Yaw L. P., Robson P., Lim B., and H.-H. Ng (2009). Eset partners with Oct4 to restrict extraembryonic trophoblast lineage potential in embryonic stem cells. Genes Dev. 23, 2507-2520.

Algar F J, Espinosa D, Moreno P, Illana J, Cerezo F, Alvarez A, Baamonde C, Redel J, Vaquero J M, Santos F, Salvatierra A. (2010). Results of lung transplantation in idiopathic pulmonary fibrosis patients. Transplant Proc. 2010 October; 42(8):3211-3213.

Balkissoon R, Lonmmatzsch S, Carolan B, Make B. Chronic obstructive pulmonary disease: a concise review. Med Clin North Am 2011; 95: 1125-41.

Barrandon Y, and Green H. Three clonal types of keratinocyte with different capacities for multiplication. Proc Natl Acad Sci USA 1987; 84: 2302-2306

Belser J A, Szretter K J, Katz J M, and Tumpey T M. Use of animal models to understand the pandemic potential of highly pathogenic avian influenza viruses. Adv Virus Res 2009; 73: 55-97

Berthiaume Y, Lesur O, Dagenais A. Treatment of adult respiratory distress syndrome: plea for rescue therapy of the alveolar epithelium. Thorax 1999; 54: 150-60

Burrows B, Fletcher C M, Heard B E, Jones N L, and Wootliff J S. The emphysematous and bronchial types of chronic airways obstruction. A clinicopathological study of patients in London and Chicago. Lancet 1966; 1: 830-835.

Camus P, Kudoh S, Ebina M. (2004). Interstitial lung disease associated with drug therapy. Br J Cancer. 2004 August; 91 Suppl 2:S18-23.

Ding B S, Nolan D J, Guo P, Babazadeh A O, Cao Z, Rosenwaks Z. et al. Endothelial-derived angiocrine signals induce and sustain regenerative lung alveolarization. Cell 2011; 147: 539-53

Fellrath J M, and du Bois R M. Idiopathic pulmonary fibrosis/cryptogenic fibrosing alveolitis. Clin Exp Med 2003; 3: 65-83; PMID: 14598183.

Gao P. Watanabe S. Ito T, Goto H, Wells K, McGregor M, et al. Biological heterogeneity, including systemic replication in mice, of H5N1 influenza A virus isolates from humans in Hong Kong. J Virol 1999; 73: 3184-3189

Günther A, Walmrath D, Grimminger F, Seeger W. (2001). Pathophysiology of acute lung injury. Semin Respir Crit Care Med. 2001 June; 22(3):247-58.

Gubareva L V, McCullers J A, Bethell R C, Webster R G. Characterization of influenza A/HongKong/156/97 (H5N1) virus in a mouse model and protective effect of zanamivir on H5N1 infection in mice. J Infect Dis 1998; 178: 1592-1596

Herridge M S, Cheung A M, Tansey C M, Matte-Martyn A. Diaz-Granados N, Al-Saidi F, et al. One-year outcomes in survivors of the acute respiratory distress syndrome. N Engl J Med 2003; 348: 683-693.

Imai Y, Kuba K, Neely G G, Yaghubian-Malhami R, Perkmann T, van Loo G, Ermolaeva M, Veldhuizen R, Leung Y H, Wang H, Liu H, Sun Y, Pasparakis M, Kopf M, Mech C, Bavari S, Peiris J S, Slutsky A S, Akira S, Hultqvist M, Holmdahl R, Nicholls J, Jiang C, Binder C J, Penninger J M. (2008). Identification of oxidative stress and Toll-like receptor 4 signaling as a key pathway of acute lung injury. Cell 133, 235-249.

Inoue A, Xin H, Suzuki T, Kanehira M, Kuroki Y, Fukuhara T, Kikuchi T, Maemondo M, Nukiwa T, Saijo Y. (2008). Suppression of surfactant protein A by an epidermal growth factor receptor tyrosine kinase inhibitor exacerbates lung inflammation. Cancer Sci. 99, 1679-1684.

Jeyaseelan S, Chu H W, Young S K, Freeman M W, Worthen G S. (2005). Distinct roles of pattern recognition receptors CD14 and Toll-like receptor 4 in acute lung injury. Infect Immun. 2005 March; 73(3): 1754-63.

Kumar P A, Hu Y, Yamamoto Y, Hoe N B, Wei T S, Mu D, et al. Distal airway stem cells yield alveoli in vitro and during lung regeneration following H1N1 influenza infection. Cell 2011; 147: 525-538

Lu X, Tumpey T M. Morken T, Zaki S R. Cox N J, and Katz J M. A mouse model for the evaluation of pathogenesis and immunity to influenza A (H5N1) viruses isolated from humans. J Virol 1999; 73, 5903-5911

Matuschak G M, and Lechner A J. Acute lung injury and the acute respiratory distress syndrome: pathophysiology and treatment. Mo Med 2010; 107: 252-258.

Moore B B, and Hogaboam C M. Murine models of pulmonary fibrosis. Am J Physiol Lung Cell Mol Physiol 2008; 294: L152-160

Mori I, Komatsu T, Takeuchi K, Nakakuki K, Sudo M, and Kimura Y. Viremia induced by influenza virus. Microb Pathog 1995; 19: 237-244

Mukhopadhyay S, Hoidal J R, Mukherjee T K. (2006). Role of TNFalpha in pulmonary pathophysiology. Respir Res. 2006 Oct. 11; 7:125.

Narasaraju T, Ng H H, Phoon M C, and Chow V T. MCP-1 antibody treatment enhances damage and impedes repair of the alveolar epithelium in influenza pneumonitis. Am J Respir Cell Mol Biol 2010; 42: 732-743

Raetz, C. and Whitfield. C. (2002) Lipopolysaccharide Endotoxins Annu. Rev. Biochem. 71-635-700.

Rheinwald J G, and Green H. Serial cultivation of strains of human epidermal keratinocytes: the formation of keratinizing colonies from single cells. Cell 1975; 6: 331-343

Senoo M., Pinto F., Crum C. P., And Mckeon F. P63 Is Essential For The Proliferative Potential Of Stem Cells Of Stratified Epithelia. Cell 2007; 129: 523-536

Suzuki H, Aoshiba K, Yokohori N, Nagai A. (2003). Epidermal growth factor receptor tyrosine kinase inhibition augments a murine model of pulmonary fibrosis. Cancer Res 63: 5054-5059.

Takada Y, Gresh L, Bozec A, Ikeda E. Kamiya K, Watanabe M. Kobayashi K, Asano K, Toyama Y, Wagner E F, Matsuo K. (2011). Interstitial lung disease induced by gefitinib and toll-like receptor ligands is mediated by Fra-1. Oncogene 30, 3821-3832.

Takahashi K, Yamanaka S. Induction of pluripotent stem cells from mouse embryonic and adult fibroblast cultures by defined factors. Cell 2007; 126: 663-76

Tammaro K A, Baldwin P D, Lundberg A S. (2005). Interstitial lung disease following erlotinib (Tarceva) in a patient who previously tolerated gefitinib (Iressa). J Oncol Pharm Pract. 2005 September; 11(3): 127-30.

Tansey C M, Louie M, Loeb M, Gold W L, Muller M P, de Jager J, et al. One-year outcomes and health care utilization in survivors of severe acute respiratory syndrome. Arch Intern Med 2007; 167: 1312-1320.

Tapscott S J, Davis R L, Thayer M J, Cheng P F, Weintraub H, Lassar A B. MyoD1: a nuclear phosphoprotein requiring a Myc homology region to convert fibroblasts to myoblasts. Science 1988; 242: 405-11

Ulich T R, Watson L R, Yin S M, Guo K Z, Wang P. Thang H et al. (1991). The intratracheal administration of endotoxin and cytokines. I. Characterization of LPS-induced IL-1 and TNF mRNA expression and the LPS-, IL-1-, and TNF-induced inflammatory infiltrate. Am J Pathol 138: 1485-1496.

Vogl T, Tenbrock K. Ludwig S, Leukert N, Ehrhardt C, van Zoelen M A et al. (2007). Mrp8 and Mrp14 are endogenous activators of Toll-like receptor 4, promoting lethal, endotoxin-induced shock. Nat Med 13: 1042-1049.

Walter N, Collard H R, King T E Jr. Current perspectives on the treatment of idiopathic pulmonary fibrosis. Proc Am Thorac Soc 2006; 3: 330-338; PMID: 16738197.

Wojcik S M, Bundman D S, and Roop D R. Delayed wound healing in keratin 6a knockout mice. Mol Cell Biol 2000; 20: 5248-5255

The contents of all references, patents and published patent applications cited throughout this application are incorporated herein by reference in their entirety.

What is claimed is:

1. A method of screening to identify agents which may be used as part of a process for causing lung regeneration, comprising
    a) providing a purified preparation of distal airway epithelial stem cells, which cells are keratin 5 (Krt5) positive and p63 positive, have mRNA levels for PLUNC (RefSeq NM_011126), SCGB3A1 (RefSeq NM_170727), GPX2 (RefSeq NM_030677), LTF (RefSeq NM_008522), SCGB3A2 (RefSeq NM_054038), CYP2F2 (RefSeq NM_007817) and/or GABRP (RefSeq NM_146017) at least ten times greater than in normal differentiated alveoli cells, can propagate for at least 50 doublings while maintaining an immature phenotype, and can differentiate into airway epithelia,
    b) contacting the distal airway epithelial stem cells with a test agent;
    c) comparing the distal airway epithelial stem cells contacted with the test agent with distal airway epithelial stem cells in the absence of the test agent and determining, relative to the distal airway epithelial stem cells in the absence of the test agent, if addition of the test agent has one or more effects on the distal airway epithelial stem cells: (i) increase viability of the airway epithelial stem cells, (ii) increase proliferation of the distal airway epithelial stem cells, (iii) increase migration of the distal airway epithelial stem cells, (iv) increase differentiation of the distal airway epithelial stem cells, and/or (v) increase secretion of paracrine factors able to prevent IL-13 mediated inflammation and/or remodeling of lung tissue.

2. The method of claim 1, wherein the distal airway epithelial stem cells are human distal airway stem cell isolated from distal airway tissue.

3. The method of claim 1, wherein the distal airway epithelial stem cells are provided as a clonal population of cells.

4. The method of claim 1, wherein the test agent is small molecule, carbohydrate, peptide or nucleic acid.

5. The method of claim 1, wherein the test agent specifically binds to a cell surface protein on the clonal population of ceils.

6. The method of claim 5, wherein the test agent is an antibody or antibody mimetic.

* * * * *